(12) United States Patent
Tanifuji et al.

(10) Patent No.: US 8,277,777 B2
(45) Date of Patent: Oct. 2, 2012

(54) COMPOUND HAVING AFFINITY FOR AMYLOID

(75) Inventors: Shigeyuki Tanifuji, Chiba (JP); Akio Hayashi, Chiba (JP); Daisaku Nakamura, Chiba (JP); Shinya Takasaki, Chiba (JP); Anthony Eamon Storey, Buckinghamshire (GB); Denis Raymond Christophe Bouvet, Buckinghamshire (GB)

(73) Assignees: Nihon Medi-Physics Co., Ltd., Tokyo (JP); GE Healthcare Limited, Little Chalfont, Buckinghamshire (GB)

( * ) Notice: Subject to any disclaimer, the term of this patent is extended or adjusted under 35 U.S.C. 154(b) by 375 days.

(21) Appl. No.: 12/308,715

(22) PCT Filed: Jun. 21, 2007

(86) PCT No.: PCT/JP2007/062503
§ 371 (c)(1),
(2), (4) Date: Dec. 16, 2009

(87) PCT Pub. No.: WO2007/148755
PCT Pub. Date: Dec. 27, 2007

(65) Prior Publication Data
US 2010/0092387 A1    Apr. 15, 2010

Related U.S. Application Data

(60) Provisional application No. 60/805,356, filed on Jun. 21, 2006.

(30) Foreign Application Priority Data

Jul. 7, 2006 (JP) ................................. 2006-188034

(51) Int. Cl.
*A61K 51/00* (2006.01)
*A61M 36/14* (2006.01)
*C07D 491/02* (2006.01)

(52) U.S. Cl. ..................... 424/1.89; 424/1.85; 424/1.81; 424/1.65; 424/1.45; 424/1.11; 546/121

(58) Field of Classification Search ................. 424/1.11, 424/1.45, 1.65, 1.81, 1.85, 1.89; 514/300; 546/121
See application file for complete search history.

(56) References Cited

U.S. PATENT DOCUMENTS

| | | | |
|---|---|---|---|
| 4,727,145 A | 2/1988 | Press | |
| 4,791,117 A | 12/1988 | Press | |
| 4,833,149 A | 5/1989 | Press | |
| 4,871,745 A | 10/1989 | Press | |
| 6,045,773 A | 4/2000 | Isakson et al. | |
| 6,562,579 B1 | 5/2003 | Yu et al. | |
| 6,596,731 B2 | 7/2003 | Mutel et al. | |
| 6,696,039 B2* | 2/2004 | Kung et al. ................. | 424/1.89 |
| 6,713,042 B2 | 3/2004 | Liu | |
| 7,264,792 B2 | 9/2007 | Gibson et al. | |
| 7,425,318 B2 | 9/2008 | Kung et al. | |
| 2001/0051632 A1 | 12/2001 | Chai et al. | |
| 2002/0006934 A1 | 1/2002 | Breitenbucher et al. | |
| 2002/0042420 A1 | 4/2002 | Briem et al. | |
| 2002/0188128 A1 | 12/2002 | Mutel et al. | |
| 2003/0212096 A1 | 11/2003 | Mutel | |
| 2005/0169837 A1 | 8/2005 | Auberson | |
| 2005/0175536 A1 | 8/2005 | Knight Castro | |
| 2005/0182059 A1 | 8/2005 | Wizenberg | |
| 2006/0051293 A1 | 3/2006 | Kung et al. | |
| 2007/0031328 A1* | 2/2007 | Kung ........................ | 424/1.11 |
| 2008/0219922 A1* | 9/2008 | Goodman et al. ........... | 424/1.65 |
| 2009/0252679 A1 | 10/2009 | Tanifuji et al. | |
| 2010/0249418 A1 | 9/2010 | Tanifuji et al. | |
| 2010/0249419 A1 | 9/2010 | Tanifuji et al. | |
| 2010/0292479 A1 | 11/2010 | Tanifuji et al. | |

FOREIGN PATENT DOCUMENTS

| | | |
|---|---|---|
| CN | 1529597 A | 9/2004 |
| JP | 63-91391 A | 4/1988 |
| JP | S63-91391 A | 4/1988 |
| JP | 2001-043978 A | 2/2001 |

(Continued)

OTHER PUBLICATIONS

Sanfilippo et al., Synthesis of (aryloxy)alkylamines. 2 Novel Imidazo-fused Heterocycles with calcium channel blocking and local Anesthetic Activity, J. Med. Chem. Nov. 1988; 31(11):2221-7.

Shah et al., Novel human histamine H3 receptor antagonists, Bioorg. Med. Chem. Lett., Nov. 18, 2002; 12(22):3309-12.

Office Action, dated Dec. 24, 2010, in corresponding Chinese Application 200780029893.0 (English translation).

C. Shah, et al. "Novel Human Histamine H3 Receptor Antagonists", Bioorganic & Medicinal Chemistry Letters 12, (2002) pp. 3309-3312.

Examination Report dated Aug. 25, 2010 issued by New Zealand Patent Office, referring to family member NZ 573363.

(Continued)

*Primary Examiner* — Michael G Hartley
*Assistant Examiner* — Leah Schlientz
(74) *Attorney, Agent, or Firm* — Fitch, Even, Tabin & Flannery, LLP

(57) ABSTRACT

A compound that has affinity with amyloid, exhibits sufficiently rapid clearance from normal tissues, and is suppressed in toxicity such as mutagenicity is provided, which is represented by the following formula (1):

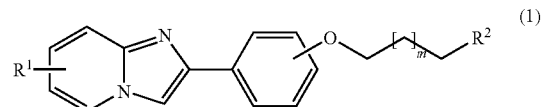

or a salt thereof,
wherein $R^1$ is a group selected from hydrogen, hydroxyl group, carboxyl group, sulfate group, amino group, nitro group, cyano group, an alkyl substituent with one to 4 carbon atoms or an alkoxy substituent with one to 4 carbon atoms; $R^2$ is a radioactive halogen substituent; and m is an integer of 0 to 2, and a low-toxic diagnostic agent for Alzheimer's disease comprising a compound represented by the above formula or a salt thereof is also provided.

12 Claims, 4 Drawing Sheets

FOREIGN PATENT DOCUMENTS

| | | | |
|---|---|---|---|
| JP | 2002-523383 A | 7/2002 |
| JP | 2004-506633 A | 3/2004 |
| JP | 2004-506723 A | 3/2004 |
| JP | 2004-525192 A | 8/2004 |
| JP | 2005-504055 A | 2/2005 |
| JP | 2005-512945 A | 5/2005 |
| JP | 2005-526749 A | 9/2005 |
| WO | WO 00/10614 A1 | 3/2000 |
| WO | 01-74813 A2 | 10/2001 |
| WO | 01-74815 A2 | 10/2001 |
| WO | WO 01/74813 A2 | 10/2001 |
| WO | WO 01/74815 A2 | 10/2001 |
| WO | WO 02/16333 A2 | 2/2002 |
| WO | WO 02/092086 A1 | 11/2002 |
| WO | WO 03/018070 A1 | 3/2003 |
| WO | WO 2004043497 A1 | 5/2004 |
| WO | WO 2005/066177 A1 | 7/2005 |
| WO | WO2007135890 A1 | 11/2007 |

OTHER PUBLICATIONS

Israel Office Action, dated Oct. 9, 2011, Ministry of Justice Patent Office, corresponding with Patent Application No. 198995.
John A. Hardy et al., "Alzheimer's Disease: The Amyloid Cascade Hypothesis", Science, vol. 256, Apr. 10, 1992, pp. 184-185.
Guy McKhann, MD et al., "Clinical diagnosis of Alzheimer's disease: Report of the NINCDS-ADRDA Work Group under the auspices of Department of Health and Human Services Task Force on Alzheimer's Disease", Neurology vol. 34, Jul. 1984, pp. 939-944.
Z.P. Zhuang et al., "Radioiodinated Styrylbenzenes and Thioflavins as Probes for Amyloid Aggregates", J. Med. Chem., vol. 44, No. 12, 2001, pp. 1905-1914.
Masahiro Ono et al., "C-labeled stilbene derivaties as AB-aggregate-specific PET imaging agents for Alzheimer's disease", Elsevier, Nuclear Medicine and Biology, vol. 30, 2003, pp. 565-571.
Hank F. Kung et al., "Novel Stilbenes as Probes for Amyloid Plaques", J. Am. Chem. Soc., vol. 123, 2001, pp. 12740-12741.
Zhi-Ping Zhuang et al., "IBOX(2-(4'-dimethylaminophenyl)-6-iodobenzoxazole): a ligand for imaging amyloid plaques in the brain", Elsevier, Nuclear Medicine and Biology, vol. 28, 2001, pp. 887-894.
S. Furumoto et al., "[11C]BF-227: A New 11C-Labeled 2-Ethenylbenzoxazole Derivative for Amyloid-B Plagues Imaging", European Journal of Nuclear Medicine and Molecular Imaging, vol. 32, Sup. 1, 2005, p. 759.
Eric D. Agdeppa, PhD et al., "2-Dialkylamino-6-Acylmalononitrile Substituted Naphthalenes (DDNP Analogs): Novel Diagnostic and Therepeutic Tools in Alzheimer's Disease", Elsevier, Molecular Imaging and Biology, vol. 5, No. 6, 2004, pp. 404-417.
Zhi-Ping Zhuang et al., "Structure-Activity Relationship of Imidazo[1,2-a]pyridines as Ligands for Detecting B-Amyloid Plagues in the Brain", J. Med. chem. vol. 46, 2003, pp. 237-243.
William E. Klunk, MD et al., "Imaging Brain Amyloid in Alzheimer's Disease with Pittsburgh Compound-B", American Neurological Association, vol. 55, No. 3, Mar. 2004, pp. 306-319.
Nicolaas P.L.G. Verhoeff, MD et al., "In-Vivo Imaging of Alzheimer Disease B-Amyloid With [11C]SB-13 PET", American Journal of Geriatric Psychiatry, vol. 12:6, 2004, pp. 584-595.
Daniel M. Skovronsky et al., "In vivo detection of amyloid plaques in a mouse model of Alzeheimer's disease", Proc. National Academy Science, vol. 97, No. 13, Jun. 20, 2000, pp. 7609-7614.
Andrew B. Newberg et al., "Safety, Biodistricution, and Dosimetry of 123I-IMPY: A Novel Amyloid Plaque-Imaging Agent for the Diagnosis of Alzheimer's Disease", The Journal of Nuclear Medicine, vol. 47, No. 5, May 2006, pp. 748-754.
Young Soo Chang et al., "Synthesis and evaluation of benzothiophene derivatives as ligands for imaging B-amyloid plaques in Alzheimer's disease", Elsevier, Nuclear Medicine and Biology, vol. 33, 2006, pp. 811-820.
Lisheng Cai et al., "Synthesis and Evaluation of Two 18F-Labeled 6-Iodo-2-(4'-N,N-dimethylamino)phenylimidazo[1,2-a]pyridine Derivatives as Prospective Radioligands for B-Amyloid in Alzheimer's Disease", Journal of Medicinal Chemistry, vol. 47, No. 9, 2004, pp. 2208-2218.
Masahiro Ono et al., Benzofuran derivatives as AB-aggregate-specific imaging agents for Alzheimer's disease, Elsevier, Nuclear Medicine and Biology, vol. 29, 2002, pp. 633-642.
Maud Hervet et al. "Comparative Study on the Reactivity of 6-Haloimidazo[1,2-a]pyridine Derivatives towards Negishi- and Stille-Coupling Reactions", Helvetica Chimica Acta, vol. 86, 2003, pp. 3461-3469.
Jerzy Lange et al., "A Structure-Activity Relationship Study of the Affinity of Selected Imidazo[1,2-a]Pyridine Derivatives, Congeners of Zolpidem, for the w1-Subtype of the Benzodiazepine Receptor" Acta Poloniae Pharamaceutica—Drug Research, vol. 58, No. 1, 2001, pp. 43-52.
Andrew Katsifis et al., "Synthesis of [123I}N',N'-Dimethyl-6-Methyl-(4'-Iodophenyl)Imidazo[1,2-a]Pyridine-3-acetamide for the Study of Peripheral Benzodiazepine Receptors using SPECT", Journal of Labelled Compounds and Radiopharmaceuticals, vol. 43, 2000, pp. 385-394.
Gordon B. Barlin et al., "Imidazo[1,2-b]pyridazines, XX*T Syntheses of Some 3-Acylaminomethyl-6-(chloro, fluoro, methoxy, methylthio, phenoxy and phenylthio)-2-(phenyl, 4-t-butylphenyl, 4-cyclohexlphenyl, B-naphthyl and styryl)imidazo[1,2-b]pyridazines and Their Interaction with Central and Peripheral-Type Benzodiazepine Receptors", Australian Journal of Chemistry, vol. 49, No. 4, 1996, pp. 451-461.
A. Katsifis et al., "Synthesis of [123I]iodine labelled imidazo[1,2-b] pyridazines as potential probes for the study of peripheral benzodiazepine receptors using SPECT", Radiochim Acta, vol. 92, 2004, pp. 305-309.
Gordon B. Barlin, "Imidazo[1,2-b]pyridazines: Syntheses and Interaction with Central and Peripheral-Type (Mitochondrial) Benzodiazepine Receptors", J. Heterocyclic Chem., vol. 35, Sep.-Oct. 1998, pp. 1205-1217.
Danqian Xu et al., Short Paper, "Synthesis of 2-arylimidazo[1,2-a]pyrimidines by the Chichibabin synthesis in ionic liquids", J. Chem, Research (S), 2003, pp. 645-647.
Sundberg et al., "Preparation of 2-Aryl and 2-Aryloxymethyl Imidazo[1, 2-a]pyridines and Related Compounds", Journal of Heterocyclic Chemistry, vol. 25, No. 1, 1988, pp. 129-137.
Enguehard et al. J. Org. Chem., vol. 68, 2003, 4367-4370.
Chandra Shah et al. "Novel Human Histamine H3 Receptor Antagonist", Bioorganic & Medicinal Chemistry Letters, vol. 12, 2002, pp. 3309-3312.
Pauline J. Sanfilippo et al., "Synthesis of (Aryloxy)alkylamines. 2. Novel Imidazo-fused Heterocycles with Calcium Channel Blocking and Local Anesthetic Activity", Journal of Medicinal Chemistry, vol. 31, No. 11, 1988, pp. 2221-2227.
International Search Report dated Dec. 4, 2007, corresponding with International Application PCT/JP2007/071121.
Chun-xiong Lu et al, Synthesis and Biodistribution of β Amyloid Plaques Imaging Agent 131I-IMPY, Journal of Nuclear and Radiochemistry, vol. 27, No. 4, pp. 232-235 (Nov. 2005), abstract at p. 235.
CN Office Action dated Nov. 24, 2011 issued against CN Appln. 200880123407.6 (see also U.S. Appl. No. 12/740,646).
Examination Report dated Sep. 26, 2011 issued against Australian Application 2007252658.
CN Office Action dated Nov. 8, 2011 issued against CN Application 200780048027.6.
Examination Reported dated Oct. 12, 2011 issued against New Zealand Application 574164.
Examination Report dated Sep. 26, 2011 issued against Australian Application 2007261985.

* cited by examiner

COMPOUND HAVING AFFINITY FOR AMYLOID

CROSS-REFERENCE TO RELATED APPLICATIONS

This is a U.S. National Phase of International Application PCT/JP2007/062503, filed Jun. 21, 2007, and claims the benefit of the filing date of U.S. Provisional Application No. 60/805,356, filed Jun. 21, 2006, and claims foreign priority under 35 U.S.C. §119 based on Japanese Application No. 2006-188034, filed Jul. 7, 2006, the entire disclosures of which applications are hereby incorporated herein by reference.

TECHNICAL FIELD

The present invention relates to a compound for use in diagnosis of cerebral degenerative disease. More specifically, the invention relates to a compound useful for amyloid detection at lesion sites in diagnosis of Alzheimer's disease and other diseases with amyloid accumulation.

BACKGROUND ART

Diseases with the onset of deposition of a fibrous protein called amyloid in various organs or tissues in bodies are generally referred to as amyloidosis. A feature common to amyloidosis is that the fibrous protein called amyloid which is enriched with the β-sheet structure is deposited at various organs systemically or at sites topically so that functional abnormalities are triggered in the organs or tissues.

Alzheimer's disease (hereinafter referred to as AD), which is a typical amyloidosis disease, is known as a disease causing dementia. This disease is lethal with progressive deposition of amyloid in brain, and thus is said to be a disease that causes concern in society compared with other amyloidosis diseases. In recent years, the number of AD patients is rapidly increasing in developed countries with aging societies, thereby causing a social problem.

From the pathohistological viewpoint, AD is characterized by three pathological findings in brain, namely development of senile plaques, formation of neurofibrillary tangles, and extensive neuronal loss. The senile plaque has a structure mainly composed of amyloid, and is said to appear at the earliest stage of AD onset and thus is pathologically found in brain about 10 or more years before appearance of clinical symptoms.

AD is diagnosed by carrying out various evaluations of cognitive functions (for example, Hasegawa scale, ADAS-JCog and MMSE) in auxiliary combination with imaging diagnosis such as CT and MRI. However, the method based on such evaluations of cognitive functions is low in diagnostic sensitivity at the early stage of the onset, and is furthermore problematic in that diagnostic results are susceptible to inborn cognitive functions of individuals. At present, it is practically impossible to establish a definite diagnosis of AD while an AD patient is still alive, because the definite diagnosis requires a biopsy of a lesion (Non-Patent Document 1).

Meanwhile, a report tells that amyloid constituting senile plaques is an aggregate of amyloid β protein (hereinafter referred to as Aβ). Also, numerous reports tell that the Aβ aggregate forms a β-sheet structure that causes nerve cell toxicity. Based on these findings, the so-called "Amyloid Cascade Hypothesis" is proposed, which suggests that cerebral deposition of Aβ triggers the downstream phenomena, namely, formation of neurofibrillary tangles and neuronal loss (Non-Patent Document 2).

Based on these facts, attempts have recently been made to detect AD in vivo using a compound having high affinity with amyloid as a marker.

Many of such probes for imaging diagnoses of cerebral amyloid are hydrophobic low-molecular compounds that are high in affinity with amyloid and high in cerebral transferability and are labeled with various radioactive species such as $^{11}C$, $^{18}F$ and $^{123}I$. For example, reports tell $^{11}C$ or radioactive halogen labeled forms of compounds including various thioflavin derivatives such as 6-iodo-2-[4'-(N,N-dimethylamino)phenyl]benzothiazole (hereinafter referred to as TZDM), and 6-hydroxy-2-[4'-(N-methylamino)phenyl]benzothiazole (hereinafter referred to as 6-OH-BTA-1) (Patent Document 1, Non-Patent Document 3); stilbene compounds such as (E)-4-methylamino-4'-hydroxystilbene (hereinafter referred to as SB-13) and (E)-4-dimethylamino-4'-iodostilbene (hereinafter referred to as m-I-SB) (Patent Document 2, Non-Patent Document 4, Non-Patent Document 5); benzoxazole derivatives such as 6-iodo-2-[4'-(N,N-dimethylamino)phenyl]benzoxazole (hereinafter referred to as IBOX) and 6-[2-(fluoro)ethoxy]-2-[2-(2-dimethylaminothiazol-5-yl)ethenyl]benzoxazole (Non-Patent Document 6, Non-Patent Document 7), DDNP derivatives such as 2-(1-{6-[(2-fluoroethyl)(methyl)amino]-2-naphthyl}ethylidene)malononitrile (hereinafter referred to as FDDNP) (Patent Document 4, Non-Patent Document 8); and imidazopyridine derivatives such as 6-iodo-2-[4'-(N,N-dimethylamino)phenyl]imidazo[1,2-a]pyridine (hereinafter referred to as IMPY) (Patent Document 3, Non-Patent Document 9). Further, some of these probes for imaging diagnosis have been studied on human imaging and have been reported to show a significant accumulation in AD patient's brain compared with normal persons (Non-Patent Document 10, Non-Patent Document 11).

[Patent Document 1] JP-T-2004-506723
[Patent Document 2] JP-T-2005-504055
[Patent Document 3] JP-T-2005-512945
[Patent Document 4] JP-T-2002-523383
[Non-Patent Document 1] J. A. Hardy & G. A. Higgins, "Alzheimer's Disease: The Amyloid Cascade Hypothesis.", Science, 1992, 256, p. 184-185
[Non-Patent Document 2] G. McKhann et al., "Clinical diagnosis of Alzheimer's disease: Report of the NINCDS-ADRDA Work Group under the auspices of Department of Health and Human Services Task Force on Alzheimer's Disease.", Neurology, 1984, 34, p. 939-944
[Non-Patent Document 3] Z.-P. Zhuang et al., "Radioiodinated Styrylbenzenes and Thioflavins as Probes for Amyloid Aggregates.", J. Med. Chem., 2001, 44, p. 1905-1914
[Non-Patent Document 4] Masahiro Ono et al., "11C-labeled stilbene derivatives as Aβ-aggregate-specific PET imaging agents for Alzheimer's disease.", Nuclear Medicine and Biology, 2003, 30, p. 565-571
[Non-Patent Document 5] H. F. Kung et al., "Novel Stilbenes as Probes for amyloid plaques.", J. American Chemical Society, 2001, 123, p. 12740-12741
[Non-Patent Document 6] Zhi-Ping Zhuang et al., "IBOX (2-(4'-dimethylaminophenyl)-6-iodobenzoxazole): a ligand for imaging amyloid plaques in the brain.", Nuclear Medicine and Biology, 2001, 28, p. 887-894
[Non-Patent Document 7] Furumoto Y et al., "[$^{11}C$]BF-227: A New $^{11}C$-Labeled 2-Ethenylbenzoxazole Derivative for Amyloid-β Plaques Imaging.", European Journal of Nuclear Medicine and Molecular Imaging, 2005, 32, Sup. 1, P759

[Non-Patent Document 8] Eric D. Agdeppa et al., "2-Dialkylamino-6-Acylmalononitrile Substituted Naphthalenes (DDNP Analogs): Novel Diagnostic and Therapeutic Tools in Alzheimer's Disease.", Molecular Imaging and Biology, 2003, 5, p. 404-417

[Non-Patent Document 9] Zhi-Ping Zhuang et al., "Structure-Activity Relationship of Imidazo[1,2-a]pyridines as Ligands for Detecting β-Amyloid Plaques in the Brain.", J. Med. Chem, 2003, 46, p. 237-243

[Non-Patent Document 10] W. E. Klunk et al., "Imaging brain amyloid in Alzheumer's disease with Pittsburgh Compound-B.", Ann. Neurol., 2004, 55, p. 306-319

[Non-Patent Document 11] Nicolaas P. L. G. Verhoeff et al., "In-Vivo Imaging of Alzheimer Disease β-Amyloid With [11C]SB-13 PET.", American Journal of Geriatric Psychiatry, 2004, 12, p. 584-595

DISCLOSURE OF THE INVENTION

Problems to be Solved by the Invention

As described above, various compounds are disclosed as probes for imaging diagnosis for amyloid, and researched for clinical application.

Experiments in normal mice show that $[^{125}I]$-labeled TZDM, IBOX and m-I-SB are all transferred into brain 2 minutes after administration. However, these compounds are insufficient in clearance from normal tissues, and tend to accumulate gradually in brain as time passes after administration (JP-T-2005-512945; Zhi-Ping Zhuang et al., Nuclear Medicine and Biology, 2001, 28, p. 887-894; H. F. Kung et al., J. Am. Chem. Soc., 2001, 123, p. 12740-12741). When the clearance from normal tissues is insufficient, a problem arises in that sufficient contrast cannot be obtained at amyloid accumulation sites. $[^{11}C]$-labeled SB-13 shows a clearance from normal tissues in experiments in rats, however, it cannot be said that the clearance is sufficiently fast (Masahiro Ono et al., Nuclear Medicine and Biology, 2003, 30, p. 565-571).

Meanwhile, it is revealed that compounds having an imidazopyridine skeleton such as IMPY have a property of transferring to brain and accumulating at amyloid after administration, and also have an excellent property of rapid clearance from normal tissues unlike the above-described compounds, as a result of experiments using $[^{125}I]$-labeled labeled compounds. However, IMPY is a compound positive in reverse mutation test. In order to use this compound as a probe for imaging diagnosis, sufficient care must be taken about dosage and administration manner. (International Publication WO03/106439 pamphlet)

FDDNP is also reported to be positive in reverse mutation test. (International Publication WO03/106439 pamphlet)

A preferable probe targeting amyloid for imaging diagnosis would be a compound that is excellent in affinity with amyloid and sufficiently rapid in clearance from normal tissues like IMPY but is suppressed in toxicity such as mutagenicity. However, no compound with such properties has been disclosed.

The present invention has been made under such circumstances, and aims at providing a compound that has affinity with amyloid, exhibits sufficiently rapid clearance from normal tissues, and is suppressed in toxicity such as mutagenicity.

Means for Solving the Problems

The inventors have found that a group of compounds satisfying the above-described requirements can be obtained by using a compound with an imidazopyridine-phenyl skeleton to which oxygen is attached at a carbon atom of the phenyl group thereof, and thus have completed the present invention.

Specifically, the present invention relates to a compound represented by the following formula (1):

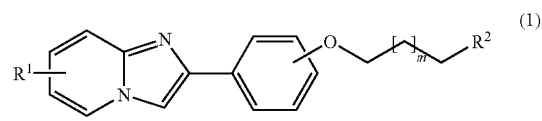

or a salt thereof, and a low-toxic diagnostic agent for Alzheimer's disease comprising a compound represented by the above formula (1) or a salt thereof.

In the formula (1), $R^1$ is a group selected from hydrogen, hydroxyl group, carboxyl group, sulfate group, amino group, nitro group, cyano group, an alkyl substituent with one to 4 carbon atoms or an alkoxy substituent with one to 4 carbon atoms. $R^1$ is preferably hydroxyl group, an alkyl substituent with one to 4 carbon atoms or an alkoxy substituent with one to 4 carbon atoms, and more preferably hydroxyl group, methyl substituent or methoxy substituent.

As $R^2$, can be used an appropriate radioactive halogen substituent, preferably a halogen selected from $^{18}F$, $^{76}Br$, $^{123}I$, $^{124}I$, $^{125}I$ or $^{131}I$, more preferably a halogen selected from $^{18}F$, $^{76}Br$, $^{123}I$ or $^{125}I$, and most preferably $^{18}F$.

Further, m is an integer of 0 to 2.

According to another aspect of the present invention, there is provided a pharmaceutical composition for in vivo imaging of amyloid deposits comprising a compound represented by the formula (1) or a salt thereof, and a pharmaceutically acceptable carrier or excipient.

According to still another aspect of the present invention, there is provided a compound represented by the formula (1) or a salt thereof for use in medicine.

According to still another aspect of the present invention, there is provided a compound represented by the formula (1) or a salt thereof for use in in vivo imaging of amyloid deposits.

According to still another aspect of the present invention, there is provided an in vivo method for detecting amyloid deposits in a subject comprising the steps of:
(a) administering a detectable quantity of a compound represented by the formula (1) or a salt thereof, and
(b) detecting the binding of the compound or the salt thereof to amyloid deposit in the subject.

According to a preferred embodiment of the present invention, the step (b) is performed by PET or SPECT imaging.

According to another aspect of the present invention, a compound represented by the following formula (2):

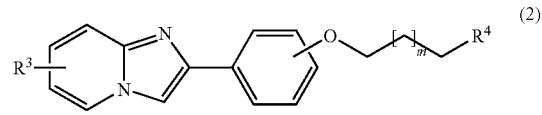

or a salt thereof is provided.

In the formula (2), $R^3$ is a group selected from hydrogen, hydroxyl group, carboxyl group, sulfate group, amino group, nitro group, cyano group, an alkyl substituent with one to 4 carbon atoms, or an alkoxy substituent with one to 4 carbon atoms. $R^3$ is preferably hydroxyl group, an alkyl substituent with one to 4 carbon atoms or an alkoxy substituent with one to 4 carbon atoms, and more preferably hydroxyl group, methyl substituent or methoxy substituent.

As $R^4$, can be used a group selected from a non-radioactive halogen substituent, methanesulfonyloxy substituent, trifluoromethanesulfonyloxy substituent or aromatic sulfonyloxy substituent.

As the non-radioactive halogen substituent, a halogen capable of being a target of nucleophilic substitution reactions using radioactive fluorine can be used, and preferably iodine or bromine can be used.

Further, m is an integer of 0 to 2.

Effects of the Invention

In accordance with the present invention, a compound that has affinity with amyloid and is sufficiently fast in clearance from normal tissues and suppressed in toxicity such as mutagenicity can be obtained as well as a diagnostic agent for Alzheimer's disease with low toxicity.

BEST MODE FOR CARRYING OUT THE INVENTION

Hereinafter, a method for synthesis of a precursor compound for a radioactive halogen-labeled compound according to an embodiment of the present invention will be described, taking the case of 6-methoxy-2-[4'-(3"-p-toluenesulfonyloxypropoxy)phenyl]imidazo[1,2-a]pyridine.

First, 2-bromo-3-hydroxypyridine is allowed to react with methyl iodide in the presence of sodium methoxide to prepare 2-bromo-3-methoxypyridine which is then subjected to nitration using a mixed acid of conc. sulfuric acid and conc. nitric acid to convert it to 2-bromo-3-methoxy-6-nitropyridine. Subsequently, the reductive elimination of the bromo group and the reduction of the nitro group using palladium-on-carbon are conducted to prepare 2-amino-5-methoxypyridine (FIG. 1, Steps 1 through 3). In the series of these reactions, reaction conditions can be determined in accordance with ordinary methods, for example, the method described in a literature, Joseph G. Lombardino, Journal of Medicinal Chemistry, 1981, 24, p. 39-42.

Separately, 4'-hydroxyacetophenone is allowed to react with cupric bromide to prepare 2-bromo-4'-hydroxyacetophenone (FIG. 1, Step 4). In this instance, reaction conditions can be set in accordance with ordinary methods, for example, the method described in a literature, King, L. Carroll and Ostrum, G. Kenneth, Journal of Organic Chemistry, 1964, 29(12), p. 3459-3461).

Then, 2-bromo-4'-hydroxyacetophenone and 2-amino-5-methoxypyridine as prepared above are allowed to react with each other to prepare 2-(4'-hydroxyphenyl)-6-methoxyimidazo[1,2-a]pyridine (FIG. 1, Step 5). This step can be done according to the following procedure.

First, 2-bromo-4'-hydroxyacetophenone and 2-amino-5-methoxypyridine are dissolved in an inactive solvent such as acetonitrile, and are allowed to react with each other at a reflux temperature for 2 to 6 hours to produce 2-(4'-hydroxyphenyl)-6-methoxyimidazo[1,2-a]pyridine hydrobromide salt as white precipitates. The inactive solvent used in this instance may be acetonitrile or another solvent that is usually employed in a similar reaction, for example, methanol and acetone. The reaction temperature may be a temperature allowing refluxing, for example, 90° C. when the solvent is acetonitrile. The amount of the solvent to be used may be an amount sufficient to effect the reaction, however, it should be noted that if the solvent is too much, it will become difficult to obtain precipitates of reaction products. For example, when 2-bromo-4'-hydroxyacetophenone in an amount corresponding to 10 mmol is used for the reaction, the amount of a solvent to be used can be about 40 to 50 mL.

Next, the reaction solution is filtered to recover the precipitates. The white precipitates are suspended in a mixed solution of methanol/water (1:1). Then, an aqueous saturated sodium hydrogencarbonate solution is added thereto in a very excessive amount relative to the suspended precipitates to release 2-(4'-hydroxyphenyl)-6-methoxyimidazo[1,2-a]pyridine as precipitates. The newly generated precipitates are filtered to recover 2-(4'-hydroxyphenyl)-6-methoxyimidazo[1,2-a]pyridine as crystals of the target compound in this step. The amount of the mixed solution of water/methanol is not specifically limited as long as it is sufficient to effect the reaction. However, it should be noted that if the amount of the mixed solution is too much, precipitation of crystals will be hindered. For example, when 2-bromo-4'-hydroxyacetophenone in an amount corresponding to 10 mmol is used, the mixed solution of water/methanol may be used in an amount of about 40 to 100 mL. The amount of sodium hydrogencarbonate is not specifically limited as long as it is very excessive relative to the above-described precipitates as the reaction substrate. For example, when the reaction is effected under the above-described conditions, the amount of an aqueous saturated sodium hydrogencarbonate solution to be added to the reaction solution can be about 25 mL.

Then, the 2-(4'-hydroxyphenyl)-6-methoxyimidazo[1,2-a]pyridine prepared above and 1,3-propanediol mono-p-toluenesulfonate are dissolved in a mixed solution of tetrahydrofuran and N,N-dimethylformamide. The mixture is then subjected to Mitsunobu reaction with addition of triphenylphosphine and diisopropylazodicarboxylate to prepare the target compound, 6-methoxy-2-[4'-(3"-p-toluenesulfonyloxypropoxy)phenyl]imidazo[1,2-a]pyridine (FIG. 1, Step 7). The other reactant 1,3-propanediol mono-p-toluenesulfonate can be easily synthesized in accordance with the method described, for example, in a literature, Abderrahim Bouzide and Gilles Sauve, Organic Letters, 2002, 4(14), p. 2329-2332 (FIG. 1, Step 6), and can be used in an excessive amount relative to the reaction substrate, typically about 2.2 times the reaction substrate 2-(4'-hydroxyphenyl)-6-methoxyimidazo[1,2-a]pyridine in molar ratio. The amounts of triphenylphosphine and diisopropylazodicarboxylate can follow the usual conditions of the Mitsunobu reaction, and are typically about equimolar to the other reactant 1,3-propanediol mono-p-toluenesulfonate.

The compound that has a hydroxyl substituent at the 6-position can be obtained by allowing 2-(4'-hydroxyphenyl)-6-methoxyimidazo[1,2-a]pyridine obtained in the step 5 to react with boron tribromide or the like for demethylation, and then protecting the hydroxyl group at the 6 position with tetrahydropyranyl group or the like, followed by the reaction of the step 7 and finally deprotection of the protective group at the 6-position. The compound that has a methyl or ethoxy substituent attached to the carbon atom at the 6-position can be obtained by using 2-amino-5-methylpyridine or 2-amino-5-ethoxypyridine instead of 2-amino-5-methoxypyridine in the step 4. At to the compound that has the substituent at another position in the imidazo[1,2-a]pyridine ring, for example, a compound having a methyl substituent or methoxy substituent attached to a carbon atom at the 8-position can be obtained by using 2-amino-3-methylpyridine or 2-amino-3-methoxypyridine instead of 2-amino-5-methoxypyridine in the step 4.

Hereinafter, a method for production of a radioactive halogen-labeled compound according to the present invention will be described, taking the case of 2-[(4'-(3"-[$^{18}$F]fluoropropoxy)phenyl]-6-methoxyimidazo[1,2-a]pyridine.

For the production of 2-[4'-(3"-[$^{18}$F]fluoropropoxy)phenyl]-6-methoxyimidazo[1,2-a]pyridine, a mixture containing an phase transfer catalyst, [$^{18}$F]fluoride ion and potassium ion is first obtained. [$^{18}$F]fluoride ion can be obtained by known methods, for example, a method in which H$_2$$^{18}$O enriched water is used as a target and exposed to proton bombardment. In this instance, the [$^{18}$F]fluoride ion exists in the H$_2$$^{18}$O enriched water used as a target. The H$_2$$^{18}$O enriched water containing the [$^{18}$F] fluoride ion is allowed to pass through an anion exchange column so that the radioactive fluorine is adsorbed and collected on the column, thereby being separated from the H$_2$$^{18}$O enriched water. Thereafter, a potassium carbonate solution is allowed to pass through the column to elute the [$^{18}$F]fluoride ion, and the eluate is supplemented with a phase transfer catalyst and is evaporated to dryness to yield a mixture containing the phase transfer catalyst, [$^{18}$F] fluoride fluoride ion and potassium ions.

Herein, various compounds having a property to form an inclusion compound with [$^{18}$F]fluoride ion can be used as the phase transfer catalyst. Specifically, various compounds for use in producing radioactive fluorine-labeled organic compounds can be used, including 18-crown-6-ether and various other aminopolyethers. In the most preferred embodiment, Kryptofix 222 (under trade name, manufactured by Merck) is used.

Then, a solution of the labeling precursor 6-methoxy-2-[4'-(3"-p-toluenesulfonyloxypropoxy)phenyl]imidazo[1,2-a]pyridine in dimethylformamide is prepared and added to the above-prepared mixture containing a phase transfer catalyst, [$^{18}$F]fluoride ion and potassium ion, and then a reaction condition is given thereto to effect, a nucleophilic substitution reaction to yield 2-[4'-(3"-[$^{18}$F]fluoropropoxy)phenyl]-6-methoxyimidazo[1,2-a]pyridine. The reaction condition can be determined according to the conditions for 2-[$^{18}$F]fluoro-2-deoxy-D-glucose and other radioactive fluorine-labeled compounds. For example, a condition may be employed, in which the reaction solution is allowed to react at about 90 to 130° C. for 5 to 10 minutes.

Other radioactive halogen-labeled compounds can be prepared by appropriately selecting a labeling precursor and a radioactive halogen to be used, and giving a reaction condition according to respective known methods. For example, 2-[4'-(3"-[$^{123}$I]iodopropoxy)phenyl]-6-methoxyimidazo[1,2-a]pyridine can be prepared by using a labeling precursor 2-[4'-(3"-chloropropoxy)phenyl]-6-methoxyimidazo[1,2-a]pyridine and subjecting it to complex decomposition reaction with Na[$^{123}$I] in a solvent of acetone or methanol.

The diagnostic agent according to the present invention can be prepared as a solution which comprises the present radioactive halogen-labeled compound blended in water, a physiological saline solution or a Ringer's solution optionally adjusted to an appropriate pH, like other commonly-known radioactive diagnostic agents. In this instance, concentration of the present compound should be adjusted to not more than the concentration at which stability of the present compound is ensured. Dosage of the present compound is not specifically limited as long as it is sufficient to obtain an image of distribution of an administered agent. For example, in case of iodine-123-labeled compounds and fluorine-18-labeled compounds, about 50 to 600 MBq per adult body of 60 kg weight can be administered intravenously or locally. Distribution of administered agents can be imaged by known methods. For example, iodine-123-labeled compounds can be imaged by a SPECT apparatus while fluorine-18-labeled compounds can be imaged by a PET apparatus.

EXAMPLE

Hereinafter, the present invention is described in more detail by way of Examples, Reference Examples and Comparative Examples. However, these Examples never limit the scope of the present invention.

In the following Examples, the names of the individual compounds are defined as shown in Table 1.

TABLE 1

| Names of compounds used for evaluation in Examples 2-4 and 5-7 | |
|---|---|
| Compound name | Common name |
| Compound 1 | 2-[4'-(3"-fluoropropoxy)phenyl]-6-methoxyimidazo[1,2-a]pyridine |
| Compound 2 | 2-[4'-(3"-fluoropropoxy)phenyl]-6-hydroxyimidazo[1,2-a]pyridine |
| Compound 3 | 2-[4'-(3"-fluoropropoxy)phenyl]imidazo[1,2-a]pyridine |
| Compound 4 | 2-[4'-(3"-[$^{18}$F]fluoropropoxy)phenyl]-6-methoxyimidazo[1,2-a]pyridine |

Reference Example 1

Synthesis of 2-[4'-(3"-fluoropropoxy)phenyl]-6-methoxyimidazo[1,2-a]pyridine (non-radioactive fluorinated form)

As a sample for evaluating affinity with amyloid, solubility in fat and mutagenicity of the present compounds, a non-radioactive fluorinated form of 2-[4'-(3"-fluoropropoxy)phenyl]-6-methoxyimidazo[1,2-a]pyridine was synthesized.

100.0 g (corresponding to 0.575 mol) of 2-bromo-3-hydroxypyridine was dissolved in 310 mL of dimethylsulfoxide, and 575 mL (corresponding to 0.575 mol) of a 1 mol/L sodium methoxide-methanol solution was added thereto. Then, the reaction solution was heated to 90° C. to distill off methanol. After the reaction solution was cooled down to 10° C. or lower, 93.9 g (corresponding to 0.662 mol) of methyl iodide was added, and then stirred at room temperature for 20.5 hours. After the completion of the reaction, the reaction solution was poured into ice water and extracted twice with chloroform. The combined chloroform layer was washed with a 1 mol/L sodium hydroxide solution, washed twice with a saturated sodium chloride solution, and dried over anhydrous sodium sulfate. After the solvent was distilled off under reduced pressure, 65.4 g (corresponding to 0.348 mol) of 2-bromo-3-methoxypyridine was obtained (FIG. 2, Step 1).

262 mL of conc. sulfuric acid was cooled down to −2° C., and 262 mL of 90% nitric acid was carefully added thereto. Subsequently, 65.3 g (corresponding to 0.347 mmol) of 2-bromo-3-methoxypyridine was carefully added thereto. After the reaction mixture was stirred in an ice bath for 10 minutes, the mixture was stirred at room temperature for 30 minutes, and then was heated to 55° C. and further stirred for 1.5 hours. After the reaction solution was cooled to room temperature, the reaction solution was poured little by little into crushed ice to generate precipitates. The precipitates were filtered and washed with water, and then dried over phosphorus pentaoxide under reduced pressure, to obtain 55.7 g (corresponding to 0.239 mol) of 2-bromo-3-methoxy-6-nitropyridine (FIG. 2, Step 2).

55.6 g (corresponding to 0.239 mol) of 2-bromo-3-methoxy-6-nitropyridine was dissolved in 1700 mL of ethanol, and 37.3 g (50% wet) of 10% palladium-carbon was added thereto under argon stream. To the mixture, 283 mL of hydrazine monohydrate was then added dropwise. After the reaction mixture was refluxed for 70 minutes, the reaction solution was cooled down to room temperature. Then, after palladium-carbon was filtered off, the residue was washed with ethanol, and the washings were combined with the filtrate. The combined solution was concentrated under reduced pressure. Then, 1300 mL of water and 130 mL of conc. aqueous ammonia were added to the concentrate, and the resulting mixture was extracted eight times with chloroform. The combined chloroform layer was dried over anhydrous sodium sulfate and concentrated under reduced pressure. The resulting crude product was distilled under reduced pressure to obtain 26.2 g (corresponding to 0.211 mol) of 2-amino-5-methoxypyridine (FIG. 2, Step 3).

50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After five hours, the reaction solution was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33 7 mmol) of 2-bromo-4'-hydroxyacetophenone (FIG. 2, Step 4).

2.15 g (corresponding to 10.0 mmol) of 2-bromo-4'-hydroxyacetophenone and 1.25 g (corresponding to 10.0 mmol) of 2-amino-5-methoxypyridine were dissolved in 50 mL, of acetonitrile. The resulting solution was refluxed in an oil bath at 90° C. for 3.5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 40 mL of water and 40 mL of methanol. Then, about 20 mL of a saturated sodium hydrogencarbonate solution was added thereto, and the mixture was sonicated for 5 minutes using a ultrasonic washing machine. Precipitates were filtered and recovered from the resulting mixture, sufficiently washed with water, and dried under reduced pressure, to obtain 1.96 g (corresponding to 8.16 mmol) of 2-(4'-hydroxyphenyl)-6-methoxyimidazo[1,2-a]pyridine (FIG. 2, Step 5).

242 mg (corresponding to 1.0 mmol) of 2-(4'-hydroxyphenyl)-6-methoxyimidazo[1,2-a]pyridine that was sufficiently dried to remove moisture was dissolved in 10 L of N,N-dimethylformamide, and 418 mg (corresponding to 3.0 mmol) of potassium carbonate was added thereto. The mixture was supplemented with 140 μL (corresponding to 1.5 mmol) of 1-bromo-3-fluoropropane, and then was stirred at room temperature for 18 hours. After the completion of the reaction, the reaction solution was poured into water and extracted three times with chloroform. The combined chloroform layer was washed once with water and once with a saturated sodium chloride solution, dried over anhydrous sodium sulfate, filtered and concentrated. The resulting crude product was purified by recycle preparative HPLC (HPLC apparatus: LC-908 (under trade name: manufactured by Japan Analytical Industry Co., Ltd.); column: two JAIGEL 2H (under trade name; manufactured by Japan Analytical Industry Co., Ltd.) connected together; mobile phase: chloroform), to obtain 189 mg (corresponding to 0.63 mmol) of 2-[4'-(3"-fluoropropoxy)phenyl]-6-methoxyimidazo[1,2-a]pyridine (hereinafter referred to as Compound 1) (FIG. 2, Step 6).

The NMR measurement results of the resulting compound (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 7.83-7.79 (m, 2H), 7.64-7.63 (s, 1H), 7.56-7.54 (m, 1H), 7.48-7.45 (m, 1H), 6.95-6.92 (m, 2H), 6.93-6.90 (m, 1H), 4.65 (dt, $^2J_{HF}$=47.0 Hz, J=6.0 Hz, 2H), 4.11 (t, J=6.0 Hz, 2H), 3.75 (s, 3H), 2.17 (dquint, $^3J_{HF}$=25.9 Hz, J=6.0 Hz, 2H).

$^{13}$C-NMR (solvent chloroform-dl; resonance frequency: 125 MHz): δ 158.48, 149.06, 145.42, 142.64, 126.93, 126.80, 119.39, 117.22, 114.58, 108.31, 107.39, 80.66 (d, $^1J_{CF}$=164.6 Hz), 63.46 (d, $^3J_{CF}$=5.8 Hz), 56.02, 30.33 (d, $^2J_{CF}$=20.2 Hz).

$^{19}$F-NMR (solvent: chloroform-dl; resonance frequency: 470 MHz): δ −221.94 (tt, $^2J_{HF}$=47.0 Hz, $^3J_{HF}$=25.9 Hz).

Reference Example 2

Synthesis of 2-[4'-(3"-fluoropropoxy)phenyl]-6-hydroxyimidazo[1,2-a]pyridine (non-radioactive fluorinated form)

As a sample for evaluating affinity with amyloid, solubility in fat and mutagenicity of the present compounds, a non-radioactive fluorinated form of 2-[4'-(3"-fluoropropoxy)phenyl]-6-hydroxyimidazo[1,2-a]pyridine was synthesized.

31.11 g (corresponding to 178.88 mmol) of 2-bromo-3-hydroxypyridine was dissolved in 95.8 mL of dimethylsulfoxide, and 89.9 mL (corresponding to 89.9 mmol) of a 1 mol/L sodium methoxide-methanol solution was added thereto. Then, the reaction solution was heated to 90° C. to distill off methanol. After the reaction solution was cooled down to 5° C. or lower, 29.2 g (corresponding to 205.62 mmol) of methyl iodide was added, and then stirred at room temperature for 17 hours. After the completion of the reaction, the reaction solution was poured into ice-water and extracted twice with chloroform. The combined chloroform layer was washed with a 1 mol/L sodium hydroxide solution, washed twice with a saturated sodium chloride solution, and dried over anhydrous sodium sulfate. After the solvent was distilled off under reduced pressure, 20.74 g (corresponding to 110.31 mmol) of 2-bromo-3-methoxypyridine was obtained (FIG. 3, Step 1).

83 mL of conc. sulfuric acid was cooled down to −5° C., and 83 mL of 90% nitric acid was carefully added thereto. Subsequently, 20.69 g (corresponding to 110.04 mmol) of 2-bromo-3-methoxypyridine was carefully added thereto. After the reaction mixture was stirred in an ice bath for 5 minutes, the mixture was stirred at room temperature for 10 minutes, and then was heated to 55° C. and further stirred for one hour. After the reaction solution was cooled to room temperature, the reaction solution was poured little by little into crushed ice to generate precipitates. The precipitates were filtered and washed with water, and then dried over phosphorus pentaoxide under reduced pressure, to obtain 17.41 g (corresponding to 74.71 mmol) of 2-bromo-3-methoxy-6-nitropyridine (FIG. 3, Step 2).

17.36 g (corresponding to 74.50 mmol) of 2-bromo-3-methoxy-6-nitropyridine was dissolved in 520 mL of ethanol, and 11.63 g (50% wet) of 10% palladium-carbon was added thereto under argon stream. To the mixture, 88.4 mL of hydrazine monohydrate was added dropwise. After the reaction mixture was refluxed for 45 minutes, the reaction solution was cooled down to room temperature. Then, after palladium-carbon was filtered off, the residue was washed with ethanol, and the washings were combined with the filtrate. The combined solution was concentrated under reduced pressure. Then, 402 mL of water and 38 mL of conc. aqueous ammonia were added to the concentrate, and the resulting mixture was extracted eight times with chloroform. The combined chloroform layer was dried over anhydrous sodium sulfate and concentrated under reduced pressure. The resulting crude product was distilled under reduced pressure to obtain 8.14 g (corresponding to 65.57 mmol) of 2-amino-5-methoxypyridine (FIG. 3, Step 3).

13.50 g (corresponding to 59.66 mmol) of 4'-benzoyloxyacetophenone was dissolved in 1100 ml of methanol, and 34.52 g (corresponding to 71.59 mmol) of tetra-n-butyl ammonium tribromide was added thereto. The mixture was stirred overnight at room temperature, and was distilled off under reduced pressure to remove the solvent. The residue was dissolved in ethyl acetate and washed twice with water and then washed with an aqueous saturated sodium chloride solution. After the ethyl acetate layer was dried over anhydrous sodium sulfate and concentrated under reduced pressure, the resulting crude product was purified by silica gel column chromatography (elution solvent: hexane/methylene chloride=1/1), to obtain 13.38 g (corresponding to 43.84 mmol) of 4'-benzoyloxy-2-bromoacetophenone (FIG. 3, Step 4).

13.33 g (corresponding to 43.68 mmol) of 4'-benzoyloxy-2-bromoacetophenone and 5.67 g (corresponding to 45.67 mmol) of 2-amino-5-methoxypyridine were dissolved in 481 mL of ethanol. The resulting solution was refluxed for 2 hours. After the reaction solution was cooled, 6.64 g (corresponding to 79.09 mmol) of sodium hydrogencarbonate was added thereto. The resulting reaction mixture was further refluxed for 4 hours. After the completion of the reaction, the solvent was concentrated under reduced pressure. The resulting residue was dissolved in chloroform and then washed with water. After the chloroform layer was dried over anhydrous sodium sulfate, the solvent was distilled off. The resulting crude product was purified by silica gel column chromatography (elution solvent: chloroform/ethyl acetate=20/1) to obtain 10.20 g (corresponding to 30.87 mmol) of 2-(4'-benzoyloxyphenyl)-6-methoxyimidazo[1,2-a]pyridine (FIG. 3, Step 5).

4.90 g (corresponding to 14.83 mmol) of 2-(4'-benzoyloxyphenyl)-6-methoxyimidazo[1,2-a]pyridine that was sufficiently dried to remove moisture was dissolved in 245 mL of chloroform and cooled down to −15° C. To this solution, a solution of 12.62 mL (corresponding to 133.48 mmol) of boron tribromide in 134 mL of dichloromethane was added dropwise. After the temperature of the resulting solution was raised to room temperature, the solution was stirred for 17 hours. After the completion of the reaction, the reaction solution was cooled with ice and supplemented with 668 mL of methanol, and further stirred at room temperature for 3 hours. The reaction mixture was then concentrated under reduced pressure. The resulting crude product was supplemented with 290 mL of chloroform and 29 mL of methanol to obtain slurry, and then precipitates were filtered and recovered. The precipitates recovered were washed with chloroform and then dried under reduced pressure, to obtain 3.00 g (corresponding to 13.28 mmol) of 2-(4'-hydroxyphenyl)-6-hydroxyimidazo[1,2-a]pyridine (FIG. 3, Step 6).

2.98 g (corresponding to 13.17 mmol) of 2-(4'-hydroxyphenyl)-6-hydroxyimidazo[1,2-a]pyridine was dissolved in 114 mL of dimethylformamide, and 2.19 g (corresponding to 15.8 mmol) of potassium carbonate was added thereto. The resulting mixture was cooled down to 4° C. To the resulting solution, a solution of 1.59 mL (corresponding to 21.08 mmol) of methoxymethyl chloride in 4.8 mL of dimethylformamide was added dropwise. After the temperature of the resulting reaction solution was raised to room temperature, the solution was stirred for 21 hours. After the completion of the reaction, the reaction solution was concentrated, and then supplemented with 57 mL of chloroform and 57 mL of methanol to obtain slurry. The slurry was filtered to separate it into the filtrate and the precipitate. The precipitate was washed with 114 mL of a mixed solution of chloroform and methanol (1:1), and was combined with the above filtrate, followed by distillation under reduced pressure. The resulting crude product was purified by silica gel column chromatography (elution solvent: chloroform/methanol=10/1 to 5/1) to obtain 2.03 g (5.78 mmol) of 2-(4'-hydroxyphenyl)-4-methoxymethyl-6-methoxymethoxyimidazo[1,2-a]pyridinium chloride (FIG. 3, Step 7).

2.01 g (corresponding to 5.73 mmol) of 2-(4'-hydroxyphenyl)-4-methoxymethyl-6-methoxymethoxyimidazo[1,2-a]pyridinium chloride was dissolved in 83.6 mL of dimethylformamide, and 3.17 g (corresponding to 22.92 mmol) of potassium carbonate and 1.62 g (corresponding to 11.46 mmol) of 1-bromo-3-fluoropropane were added thereto. The mixture was stirred overnight at room temperature. After the completion of the reaction, the reaction solution was poured into water and extracted twice by a salting-out extraction procedure using chloroform with addition of sodium chloride. The combined chloroform layer was washed with a saturated sodium chloride solution, dried over anhydrous magnesium sulfate and concentrated. The resulting crude product was purified by silica gel column chromatography (elution solvent: chloroform/methanol=10/1 to 5/1), to obtain 1.95 g (corresponding to 4.57 mmol) of 2-[4'-(3"-fluoropropoxy)phenyl]-4-methoxymethyl-6-methoxymethoxyimidazo[1,2-a]pyridinium chloride (FIG. 3, Step 8).

1.93 g (corresponding to 4.53 mmol) of 2-[4'-(3"-fluoropropoxy)phenyl]-4-methoxymethyl-6-methoxymethoxyimidazo[1,2-a]pyridinium chloride was dissolved in 29 mL of methanol, and 0.95 mL of conc. hydrochloric acid was added thereto. Then, the mixture was refluxed for 2 hours. After the reaction solution was cooled, the solution was poured into water, and extracted twice by a salting-out extraction procedure using chloroform with addition of sodium chloride. The combined chloroform layer was dried over anhydrous magnesium sulfate and concentrated. The resulting crude product was purified by silica gel column chromatography (elution solvent: chloroform/methanol=10/1 to 5/1), to obtain 1.22 g (corresponding to 3.68 mmol) of 2-[4'-(3"-fluoropropoxy)phenyl]-6-methoxymethoxyimidazo[1,2-a]pyridine (FIG. 3, Step 9).

1.18 g (corresponding to 3.57 mmol) of 2-[4'-(3"-fluoropropoxy)phenyl]-6-methoxymethoxyimidazo[1,2-a]pyridine was dissolved in 29 mL of isopropyl alcohol, and 0.59 mL of conc. hydrochloric acid was added thereto. Then, the mixture was refluxed for 23 hours. After the reaction solution was cooled, the solution was poured into water, and extracted twice by a salting-out extraction procedure using chloroform with addition of sodium chloride. The combined chloroform layer was dried over anhydrous magnesium sulfate. The resulting crude product was purified by silica gel column chromatography (elution solvent: chloroform/methanol=10/1), to obtain 481 mg (corresponding to 1.68 mmol) of 2-[4'-(3"-fluoropropoxy)phenyl]-6-hydroxyimidazo[1,2-a]pyridine (hereinafter referred to as Compound 2) (FIG. 3, Step 10).

The NMR measurement results of the resulting compound (internal standard: dimethylsulfoxide) are shown below.

NMR apparatus employed: JNM-GSX-270 (manufactured by Japan Electron Optics Laboratory Co., Ltd. (JEOL))

$^1$H-NMR (solvent: dimethylsulfoxide-d6; resonance frequency: 270 MHz): δ 8.52 (s, 2H), 8.30-8.25 (m, 1H), 7.85-7.79 (m, 1H), 7.67-7.62 (m, 1H), 7.22-7.16 (m, 2H), 5.64 (s, 1H), 4.62 (dt, $^2J_{HF}$=47.0 Hz, J=5.9 Hz, 2H), 4.17 (t, J=5.9 Hz, 2H), 2.14 (dquint, $^3J_{HF}$=26.2 Hz, J=5.9 Hz, 2H).

Reference Example 3

Synthesis of 2-[4'-(3"-fluoropropoxy)phenyl]imidazo[1,2-a]pyridine (non-radioactive fluorinated form)

As a sample for evaluating affinity with amyloid, solubility in fat and mutagenicity of the present compounds, a non-radioactive fluorinated form of 2-[4'-(3"-fluoropropoxy)phenyl]imidazo[1,2-a]pyridine was synthesized.

50 mL of ethyl acetate was added to 28.17 g (corresponding to 126 mmol) of cupric bromide to obtain a suspension, and a solution of 8.18 g (corresponding to 60.0 mmol) of 4'-hydroxyacetophenone in a mixed solution of 50 mL of ethyl acetate and 50 mL of chloroform was added thereto. Then, the mixture was refluxed. After five hours, the reaction mixture was cooled to room temperature and filtered. The resulting filtrate was concentrated under reduced pressure. The residue was dissolved in ethyl acetate and subjected to decoloring operation with addition of active charcoal. Then, solution was filtered and concentrated. The resulting crude product was purified by flash silica gel column chromatography (elution solvent: chloroform/methanol=20/1), and then recrystallized from ethyl acetate/petroleum ether, to obtain 7.25 g (corresponding to 33.7 mmol) of 2-bromo-4'-hydroxyacetophenone (FIG. 4, Step 1).

649 mg (corresponding to 3.0 mmol) of 2-bromo-4'-hydroxyacetophenone and 285 mg (corresponding to 3.0 mmol) of 2-aminopyridine were dissolved in 20 mL of acetonitrile. The resulting solution was refluxed in an oil bath at 110° C. for one hour. After the reaction solution was cooled down to room temperature, 254 mg (corresponding to 5.4 mmol) of sodium hydrogencarbonate was added thereto. The resulting mixture was refluxed in an oil bath at 100° C. for one hour. After the completion of the reaction, the reaction solution was cooled to room temperature, and precipitates were filtered and recovered therefrom. The precipitates were washed with acetonitrile and water, and then dried under reduced pressure to obtain 405 mg (corresponding to 1.9 mmol) of 2-(4'-hydroxyphenyl)imidazo[1,2-a]pyridine (FIG. 4, Step 2).

398 mg (corresponding to 1.89 mmol) of 2-(4'-hydroxyphenyl)imidazo[1,2-a]pyridine was dissolved in 15 mL of N,N-dimethylformamide, and 788 mg (corresponding to 5.7 mmol) of potassium carbonate was added thereto. 260 μL (corresponding to 2.8 mmol) of 1-bromo-3-fluoropropane was added to the resulting mixture, and the mixture was stirred for 20.5 hours at room temperature. After the completion of the reaction, the reaction solution was poured into water and extracted three times with chloroform. The combined chloroform layer was washed with water and a saturated sodium chloride solution, and then dried over anhydrous sodium sulfate, filtered and concentrated. The resulting crude product was purified by recycle preparative HPLC (HPLC apparatus: LC-908 (under trade name; manufactured by Japan Analytical Industry Co., Ltd.); column: two of JAI-GEL 2H (under trade name; manufactured by Japan Analytical Industry Co., Ltd.) connected together; mobile phase: chloroform), to obtain 264 mg (corresponding to 0.98 mmol) of 2-[4'-(3"-fluoropropoxy)phenyl]imidazo[1,2-a]pyridine (hereinafter referred to as Compound 3) (FIG. 4, Step 3).

The NMR measurement results of the resulting compound (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 8.09 (dt, J=6.9, 1.2 Hz, 1H), 7.90-7.86 (m, 2H), 7.76 (d, J=0.7 Hz, 1H), 7.62-7.59 (m, 1H), 7.14 (ddd, J=9.1, 6.7, 1.2 Hz, 1H), 6.99-6.95 (m, 2H), 6.75 (dt, J=6.7, 1.2 Hz, 1H), 4.67 (dt, $^2J_{HF}$=47.0 Hz, J=6.0 Hz, 2H), 4.14 (t, J=6.0 Hz, 2H), 2.19 (dquint., $^3J_{HF}$=25.9 Hz, J=6.0 Hz, 2H).

$^{13}$C-NMR (solvent: chloroform-dl; resonance frequency: 125 MHz): δ 158.74, 145.68, 145.61, 127.29, 126.67, 125.42, 124.41, 117.29, 114.69, 112.21, 107.21, 80.73 (d, $^1J_{CF}$=164.6 Hz), 63.53 (d, $^3J_{CF}$=5.3 Hz), 30.42 (d, $^2J_{CF}$=20.2 Hz).

$^{19}$F-NMR (solvent: chloroform-dl; resonance frequency: 470 MHz): δ −222.04 (dd, $^2J_{HF}$=47.0 Hz, $^3J_{HF}$=25.9 Hz).

Reference Example 4

Synthesis of 2-[4'-(3"-fluoropropoxy)phenyl]-6-iodoimidazo[1,2-a]pyridine (non-radioactive fluorinated form)

For the purpose of preparing a calculation formula for use in the calculation of log $P_{HPLC}$ of the present compound, a non-radioactive fluorinated form of 2-[4'-(3"-fluoropropoxy)phenyl]-6-iodoimidazo[1,2-a]pyridine was synthesized.

50 mL of ethyl acetate was added to 28.17 g (corresponding to 126 mmol) of cupric bromide to obtain a suspension, and a solution of 8.18 g (corresponding to 60.0 mmol) of 4'-hydroxyacetophenone in a mixed solution of 50 mL ethyl acetate and 50 mL of chloroform was added thereto. Then, the mixture was refluxed. After five hours, the reaction solution was cooled to room temperature and filtered. The resulting filtrate was concentrated under reduced pressure. After the residue was dissolved in ethyl acetate and subjected to decoloring operation with addition of active charcoal, the solution was filtered and concentrated. The resulting crude product was purified by flash silica gel column chromatography (elution solvent: chloroform/methanol=20/1), and then recrystallized from ethyl acetate/petroleum ether, to obtain 7.25 g (corresponding to 33.7 mmol) of 2-bromo-4'-hydroxyacetophenone (FIG. 5, Step 1).

441 mg (corresponding to 2.0 mmol) of 2-bromo-4'-hydroxyacetophenone and 449 mg (corresponding to 2.0 mmol) of 2-amino-5-iodopyridine were dissolved in 15 mL of acetonitrile. The resulting solution was refluxed in an oil bath at 110° C. for 5 hours. After the completion of the reaction, the reaction solution was cooled down to room temperature, and precipitates were filtered and recovered. The precipitates were washed with acetonitrile, and dried under reduced pressure. The resulting crude crystals were suspended in a mixed solution of 10 mL of water and 10 mL of methanol, and then supplemented with about 10 mL of a saturated sodium hydrogencarbonate solution and sonicated for 5 minutes using an ultrasonic washing machine. Precipitates were filtered and recovered from the resulting mixture, sufficiently washed with water, and dried under reduced pressure, to obtain 526 mg (corresponding to 1.56 mmol) of 2-(4'-hydroxyphenyl)-6-iodoimidazo[1,2-a]pyridine (FIG. 5, Step 2).

673 mg (corresponding to 2.0 mmol) of 2-(4'-hydroxyphenyl)-6-iodoimidazo[1,2-a]pyridine was dissolved in 25 mL of N,N-dimethylformamide, and 831 mg (corresponding to 6.0 mmol) of potassium carbonate was added thereto. 275 μL (corresponding to 3.0 mmol) of 1-bromo-3-fluoropropane was added to the resulting solution, and the solution was stirred for 24 hours at room temperature. After the completion of the reaction, the reaction solution was poured into water, and extracted three times with chloroform. The combined chloroform layer was washed with water and a saturated sodium chloride solution, dried over anhydrous sodium sulfate, filtered and concentrated. The resulting crude product was purified by flash silica gel column chromatography (elution solvent: chloroform), and further purified by recycle preparative HPLC (HPLC apparatus: LC-908 (under trade name; manufactured by Japan Analytical Industry Co., Ltd.); column: two of JAIGEL 2H (under trade name; manufactured by Japan Analytical Industry Co., Ltd.) connected together; mobile phase: chloroform), to obtain 349 mg (corresponding to 0.881 mmol) of 2-[4'-(3"-fluoropropoxy)phenyl]-6-iodoimidazo[1,2-a]pyridine (FIG. 5, Step 3).

The NMR measurement results of the resulting compound (internal standard substance: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 8.37-8.35 (m, 1H), 7.88-7.84 (m, 2H), 7.72 (s, 1H), 7.42-7.39 (m, 1H), 7.32 (dd, J=9.4, 1.6 Hz, 1H), 6.99-6.96 (m, 2H), 4.67 (dt, $^2J_{HF}$=47.0 Hz, J=6.0 Hz, 2H), 4.15 (t, J=6.0 Hz, 2H), 2.20 (dquint, $^3J_{HF}$=25.9 Hz, J=6.0 Hz, 2H).

$^{13}$C-NMR (solvent: chloroform-dl, resonance frequency: 125 MHz): δ 159.01, 146.23, 144.16, 132.36, 130.28, 127.42, 126.05, 118.31, 114.77, 106.90, 80.72 (d, $^1J_{CF}$=164.6 Hz), 74.80, 63.57 (d, $^3J_{CF}$=5.3 Hz), 30.42 (d, $^2J_{CF}$=20.2 Hz).

$^{19}$F-NMR (solvent: chloroform-dl, resonance frequency: 470 MHz): δ 222.09 (dd, $^2J_{HF}$=47.0 Hz, $^3J_{HF}$=25.9 Hz).

Reference Example 5

Synthesis of 2-(4'-hydroxyphenyl)-6-iodoimidazo[1,2-a]pyridine

For the purpose of preparing a calculation formula for use in the calculation of log $P_{HPLC}$ of the present compound, a non-fluorinated form of 2-(4'-hydroxyphenyl)-6-iodoimidazo[1,2-a]pyridine was synthesized.

50 mL of ethyl acetate was added to 28.17 g (corresponding to 126 mmol) of cupric bromide to obtain a suspension, and a solution of 8.18 g (corresponding to 60.0 mmol) of 4'-hydroxyacetophenone in a mixed solution of 50 mL of ethyl acetate and 50 mL of chloroform was added thereto. Then, the mixture was refluxed. After five hours, the reaction solution was cooled to, room temperature and filtered. The resulting filtrate was concentrated under reduced pressure. The residue was dissolved in ethyl acetate, and subjected to decoloring operation with addition of active charcoal. The solution was filtered and concentrated. The resulting crude product was purified by flash silica gel column chromatography (elution solvent: chloroform/methanol=20/1). The product was then recrystallized from ethyl acetate/petroleum ether, to obtain 7.25 g (corresponding to 33.7 mmol) of 2-bromo-4'-hydroxyacetophenone (FIG. 6, Step 1).

441 mg (corresponding to 2.0 mmol) of 2-bromo-4'-hydroxyacetophenone and 449 mg (corresponding to 2.0 mmol) of 2-amino-5-iodopyridine were dissolved in 15 mL of acetonitrile. The resulting solution was refluxed in an oil bath at 110° C. for 5 hours. After the completion of the reaction, the reaction solution was cooled down to room temperature, and precipitates were filtered and recovered. The precipitates were washed with acetonitrile, and dried under reduced pressure. The resulting crude crystals were suspended in a mixed solution of 10 mL of water and 10 mL of methanol. The suspension was supplemented with about 10 mL of a saturated sodium hydrogencarbonate solution, and was sonicated for 5 minutes with an ultrasonic washing machine. Precipitates were filtered and recovered from the resulting mixture, washed with water, and dried under reduced pressure, to obtain 526 mg (corresponding to 1.56 mmol) of 2-(4'-hydroxyphenyl)-6-iodoimidazo[1,2-a]pyridine (FIG. 6, Step 2).

The NMR results of the obtained 2-(4'-hydroxyphenyl)-6-iodoimidazo[1,2-a]pyridine (internal standard substance: dimethylsulfoxide) are shown below.

NMR apparatus employed: JNM-ECP-500 (manufactured by Japan Electron Optics Laboratory Co., Ltd. (JEOL))

$^1$H-NMR (solvent: dimethylsulfoxide-d6; resonance frequency: 500 MHz): δ 8.86-8.84 (m, 1H), 8.14 (s, 1H), 7.78-7.74 (m, 2H), 7.40-7.35 (m, 2H), 6.86-6.82 (m, 2H).

$^{13}$C-NMR (solvent: dimethylsulfoxide-d6; resonance frequency: 125 MHz): δ 158.08, 145.87, 143.87, 132.48, 131.72, 127.67, 124.99, 118.14, 116.14, 108.02, 75.85.

Reference Example 6

Synthesis of [$^{125}$I]-2-(4'-(3"-fluoropropoxy)phenyl-6-iodoimidazo[1,2-a]pyridine For the purpose of preparing a calculation formula for use in the calculation of log $P_{HPLC}$ of the present compound, [$^{125}$I]-2-(4'-(3"-fluoropropoxy)phenyl-6-iodoimidazo[1,2-a] pyridine was synthesized in accordance with the following steps.

50 mL of ethyl acetate was added to 28.17 g (corresponding to 126 mmol) of cupric bromide to obtain a suspension, and a solution of 8.18 g (corresponding to 60.0 mmol) of 4'-hydroxyacetophenone in a mixed solution of 50 mL of ethyl acetate and 50 mL of chloroform was added thereto. Then, the mixture was refluxed. After five hours, the reaction mixture was cooled to room temperature and filtered. The resulting filtrate was concentrated under reduced pressure. After the residue was dissolved in ethyl acetate and subjected to decoloring operation with addition of active charcoal, the solution was filtered and concentrated. The resulting crude product was purified by flash silica gel column chromatography (elution solvent: chloroform/methanol=20/1), and then recrystallized from ethyl acetate/petroleum ether to obtain 7.25 g (corresponding to 33.7 mmol) of 2-bromo-4'-hydroxyacetophenone (FIG. 7, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was refluxed in an oil bath at 105° C. for 6 hours. After the completion of the reaction, the reaction solution was cooled down to room temperature, and precipitates were filtered and recovered. The precipitates were washed with acetonitrile, and dried under reduced pressure. The resulting crude crystals were suspended in a mixed solution of 20 mL of water and 20 mL of methanol, and then supplemented with about 25 mL of a saturated sodium hydrogencarbonate solution and sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a]pyridine (FIG. 7, Step 2).

290 mg (corresponding to 1.0 mmol) of 6-bromo-2-(4'-hydroxyphenyl)imidazo[1,2-a]pyridine that was sufficiently dried to remove moisture was dissolved in 10 mL of N,N-dimethylformamide, and 413 mg (corresponding to 3.0 mmol) of potassium carbonate was added thereto. 138 µL (corresponding to 1.5 mmol) of 1-bromo-3-fluoropropane was added to the resulting solution, and then the solution was stirred at room temperature for 20.5 hours. After the completion of the reaction, the reaction solution was poured into water and extracted three times with chloroform. The combined chloroform layer was washed with a saturated sodium chloride solution, dried over anhydrous sodium sulfate, and filtered and concentrated. The resulting crude product was purified by recycle preparative HPLC (HPLC apparatus: LC-908 (under trade name; manufactured by Japan Analytical Industry Co., Ltd.); column: two of JAIGEL 2H (under trade name; manufactured by Japan Analytical Industry Co., Ltd.) connected together; mobile phase: chloroform), to obtain 302 mg (corresponding to 0.866 mmol) of 6-bromo-2-[4'-(3"-fluoropropoxy)phenyl]imidazo[1,2-a]pyridine (FIG. 7, Step 3).

85 mg (corresponding to 0.24 mmol) of 6-bromo-2-[4'-(3"-fluoropropoxy)phenyl]imidazo[1,2-a]pyridine was dissolved in 10 mL of dioxane, and 2 mL of triethylamine was added thereto. Then, 185 µL (corresponding to 0.36 mmol) of bistributyltin and 20 mg (at a catalytic amount) of tetrakis-triphenylphosphine palladium were added thereto. After the reaction mixture was stirred at 90° C. for 24 hours, the solvent was distilled off under reduced pressure. The residue was purified by preparative TLC (elution solvent: hexane/ethyl acetate=6/4). Further, the resulting crude product was purified by recycle preparative HPLC (HPLC apparatus: LC-908 (under trade name; manufactured by Japan Analytical Industry Co., Ltd.); column: two of JAIGEL 2H (under trade name; manufactured by Japan Analytical Industry Co., Ltd.) connected together; mobile phase: chloroform), to obtain 42 mg (corresponding to 74.2 µmol) of 6-tributylstannyl-2-[4'-(3"-fluoropropoxy)phenyl]imidazo[1,2-a]pyridine (FIG. 7, Step 4).

The NMR measurement results of the obtained 6-tributylstannyl-2-[4'-(3"-fluoropropoxy)phenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl; resonance frequency: 500 MHz): δ 8.01-7.93 (m, 1H), 7.91-7.87 (m, 2H), 7.75-7.74 (m, 1H), 7.63-7.58 (m, 1H), 7.20-7.11 (m, 1H), 7.00-6.95 (m, 2H), 4.67 (dt, $J_{HF}$=47.0 Hz, J=6.0 Hz, 2H), 4.15 (t, J=6.0 Hz, 2H), 2.20 (dquint, $J_{HF}$=26.1 Hz, J=6.0 Hz, 2H), 1.64-1.47 (m, 6H), 1.39-1.31 (m, 6H), 1.19-1.04 (m, 6H), 0.91 (t, J=7.2 Hz, 9H).

To 100 µL of a solution of 6-tributylstannyl-2-[4'-(3"-fluoropropoxy)phenyl]imidazo[1,2-a]pyridine in methanol (at a concentration of 1 mg/mL), 50 µL of 1 mol/L hydrochloric acid, 10 to 100 µL of [$^{125}$I]sodium iodide of 37-370 MBq and 20 µL of 10% (w/v) hydrogen peroxide were added. After the mixed solution was left to stand at ambient temperature for 10 minutes, the solution was subjected to HPLC under the following conditions, to obtain [$^{125}$I]-2-(4'-(3"-fluoropropoxy)phenyl-6-iodoimidazo[1,2-a]pyridine fraction (FIG. 7, Step 5).

HPLC conditions:

Column: Phenomenex Luna C18 (trade name; manufactured by Phenomenex Co.; size: 4.6×150 mm)

Mobile phase: 0.1% trifluoroacetic acid/acetonitrile containing 0.1% trifluoroacetic acid=80/20 to 0/100 (17 minutes)

Flow rate: 1.0 mL/min.

Detector: Ultraviolet visible absorptiometer (Detection wavelength: 282 nm) and radioactivity counter (manufactured by raytest: type STEFFI)

10 ml of water was added to the fraction. The resulting solution was passed through Sep-Pak C18 column (trade name: Sep-Pak (registered trademark) Light C18 Cartridges manufactured by Waters: the packed amount of the packing agent: 130 mg) so that the column adsorbs and collects [$^{125}$I]-2-(4'-(3"-fluoropropoxy)phenyl-6-iodoimidazo[1,2-a]pyridine. The column was rinsed with 1 mL of water, and then 1 mL of ethanol was passed therethrough to elute [$^{125}$I]-2-(4'-(3"-fluoropropoxy)phenyl-6-iodoimidazo[1,2-a]pyridine.

The amount of radioactivity of the obtained compound was 37.5 MBq at the end of synthesis. Further, the TLC analysis was determined under the following conditions, and as a result, the radiochemical purity of the compound was 96.5%.

TLC analysis conditions:

TLC plate: RP-18F254 (trade name; manufactured by Merck & Co., Inc.)

Mobile phase: Methanol/water=20/1

Detector: Bio-imaging Analyzer BAS 2500 (type: BAS-2500 manufactured by FUJIFILM Corporation)

Reference Example 7

Synthesis of [$^{125}$I]-2-(4'-hydroxyphenyl)-6-iodoimidazo[1,2-a]pyridine

For the purpose of preparing a calculation formula for use in the calculation of log $P_{HPLC}$ [$^{125}$I]-2-(4'-hydroxyphenyl)-6-iodoimidazo[1,2-a]pyridine was synthesized in accordance with the following steps.

50 mL of ethyl acetate was added to 28.17 g (corresponding to 126 mmol) of cupric bromide to obtain a suspension, and a solution of 8.18 g (corresponding to 60.0 mmol) of 4'-hydroxyacetophenone in a mixed solution of 50 mL of ethyl acetate and 50 mL of chloroform was added thereto. Then, the mixture was refluxed. After five hours, the reaction mixture was cooled to room temperature and filtered. The resulting filtrate was concentrated under reduced pressure. After the residue was dissolved in ethyl acetate and subjected to decoloring operation with addition of active charcoal, the solution was filtered and concentrated. The resulting crude product was purified by flash silica gel column chromatography (elution solvent: chloroform/methanol=20/1), and then recrystallized from ethyl acetate/petroleum ether to obtain 7.25 g (corresponding to 33.7 mmol) of 2-bromo-4'-hydroxyacetophenone (FIG. 8, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was refluxed in an oil bath at 105° C. for 6 hours. After the completion of the reaction, the reaction solution was cooled down to room temperature, and precipitates were filtered and recovered. The precipitates were washed with acetonitrile, and dried under reduced pressure. The resulting crude crystals were suspended in a mixed solution of 20 mL of water and 20 mL of methanol, and then supplemented with about 25 mL of a saturated sodium hydrogencarbonate solution and sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a]pyridine (FIG. 8, Step 2).

138 mg (corresponding to 0.476 mmol) of 6-bromo-2-(4'-hydroxyphenyl)imidazo[1,2-a]pyridine was dissolved in 20 mL of dioxane, and 2 mL of triethylamine was added thereto. Then, 360 µL (corresponding to 0.713 mmol) of bistributyl tin and 20 mg (at a catalytic amount) of tetrakis-triphenylphosphine palladium were added. After the reaction mixture was stirred at 90° C. for 22 hours, the solvent was distilled off under reduced pressure. The residue was purified by preparative TLC (elution solvent: hexane/ethyl acetate=1/4). Further, the resulting crude product was purified by recycle preparative HPLC (HPLC apparatus: LC-908 (under trade name, manufactured by Japan Analytical Industry Co., Ltd.); column: two of JAIGEL 2H (under trade name; manufactured by Japan Analytical Industry Co., Ltd.) connected together; mobile phase: chloroform), to obtain 47 mg (corresponding to 94.9 μmol) of 6-tributylstannyl-2-(4'-hydroxyphenyl)imidazo[1,2-a]pyridine (FIG. 8, Step 3).

To 53 μL of a solution of 6-tributylstannyl-2-(4'-hydroxyphenyl)imidazo[1,2-a]pyridine in methanol (at a concentration of 1 mg/mL), 50 μL of 1 mol/L hydrochloric acid, [$^{125}$I] sodium iodide of 136 MBq (40 μL in volume) and 10 μL of 10% (w/v) hydrogen peroxide were added. After the mixed solution was left to stand at 50° C. for 10 minutes, the solution was subjected to HPLC under the same conditions as described in Reference Example 6, to obtain [$^{125}$I]-2-(4'-hydroxyphenyl)-6-iodoimidazo[1,2-a]pyridine fraction (FIG. 8, Step 4).

10 ml of water was added to the fraction. The resulting solution was passed through a reverse phase column (trade name: Sep-Pak (registered trademark) Light C18 Cartridges manufactured by Waters; the packed amount of the packing agent: 130 mg), so that the column adsorbs and collects the [$^{125}$I]-2-(4'-hydroxyphenyl)-6-iodoimidazo[1,2-a]pyridine. The column was rinsed with 1 mL of water, and then 1 mL of ethanol was passed therethrough, to elute [$^{125}$I]-2-2 (4'-hydroxyphenyl)-6-iodoimidazo[1,2-a]pyridine. The obtained radioactivity was 37.5 MBq at the end of synthesis. Further, the TLC analysis was determined under the same conditions as described in Reference Example 6, and as a result, the radiochemical purity of the compound was 96.5%.

Reference Example 8

Synthesis of [$^{123}$I]-IMPY

[$^{123}$I]-IMPY was prepared in accordance with the following steps for use in Comparative Examples for evaluations on Log $P_{octanol}$ and accumulation in brain.

In accordance with the method described in a literature (Zhi-Ping Zhuang et al., J. Med. Chem., 2003, 46, p. 237-243), 6-tributylstannyl-2-[4'-(N,N-dimethylamino)phenyl] imidazo[1,2-a]pyridine was synthesized, and dissolved in methanol (concentration: 1 mg/mL). To 53 μL of the resulting solution, 100 μL of 1 mol/L hydrochloric acid, 20-50 μL of [$^{123}$I]sodium iodide of 190-240 MBq, 10 μL of a 1 mmol/L sodium iodide and 10 μL of 10% (w/v) hydrogen peroxide were added. After the mixed solution was left to stand at 50° C. for 10 minutes, the solution was subjected to HPLC under the same conditions as described in Reference Example 4, to obtain [$^{123}$I]-IMPY fraction.

10 ml of water was added to the fraction. The resulting solution was passed through a reverse phase column (trade name: Sep-Pak (registered trademark) Light C18 Cartridges manufactured by Waters; the packed amount of the packing agent: 130 mg), so that the column adsorbs and collects the [$^{123}$I]-IMPY. The column was rinsed with 1 mL of water, and then 1 mL of ethanol was passed therethrough, to elute [$^{123}$I]-IMPY. The obtained radioactivity was 47-56 MBq at the end of synthesis. Further, the TLC analysis was determined under the same conditions as described in Reference Example 4, and as a result, the radiochemical purity of the compound was 98.0%.

Example 1

Synthesis of 6-methoxy-2-[4'-(3"-p-toluenesulfonyloxypropoxy)phenyl]imidazo[1,2-a]pyridine 100.0 g (corresponding to 0.575 mol) of 2-bromo-3-hydroxypyridine was dissolved in 310 mL of dimethylsulfoxide, and 575 mL (corresponding to 0.575 mol) of a solution of 1 mol/L sodium methoxide in methanol was added thereto. Then, the reaction solution was heated to 90° C. to distill off methanol. After the reaction solution was cooled down to 10° C. or lower, 93.9 g (corresponding to 0.662 mol) of methyl iodide was added thereto, and the mixture was stirred at room temperature for 20.5 hours. After the completion of the reaction, the reaction solution was poured into ice water and extracted twice with chloroform. The combined chloroform layer was washed with a 1 mol/L sodium hydroxide solution, washed twice with a saturated sodium chloride solution, and dried over anhydrous sodium sulfate. Then, the solvent was distilled off under reduced pressure, to obtain 65.4 g (corresponding to 0.348 mol) of 2-bromo-3-methoxypyridine (FIG. 1, Step 1).

262 mL of conc. sulfuric acid was cooled down to −2° C., and 262 mL of 90% nitric acid was carefully added thereto. Then, 65.3 g (corresponding to 0.347 mmol) of 2-bromo-3-methoxypyridine was carefully thereto. After the resulting mixture was stirred in an ice bath for 10 minutes, the mixture was stirred at room temperature for 30 minutes. Then, after the temperature of the mixture was raised up to 55° C., the mixture was stirred for 1.5 hours. After the reaction solution was cooled down, the reaction solution was poured little by little onto crushed ice to generate precipitates. The precipitates were filtered and washed with water. The precipitates obtained was dried over phosphorus pentaoxide under reduced pressure to obtain 55.7 g (corresponding to 0.239 mol) of 2-bromo-3-methoxy-6-nitropyridine (FIG. 1, Step 2).

55.6 g (corresponding to 0.239 mol) of 2-bromo-3-methoxy-6-nitropyridine was dissolved in 1700 mL of ethanol, and 37.3 g (50% wet) of 10% palladium-carbon was added thereto under argon stream. Then, 283 mL of hydrazine monohydrate was added dropwise. After the reaction mixture was refluxed for 70 minutes, the reaction solution was cooled down to room temperature. Then, palladium-carbon was filtered off, which was then washed with ethanol. The washings were combined with the filtrate. After the resulting solution was concentrated under reduced pressure, the concentrate was supplemented with 1300 mL of water and 130 mL of conc. aqueous ammonia, and extracted eight times with chloroform. The combined chloroform layer was dried over anhydrous sodium sulfate and concentrated under reduced pressure. The resulting crude product was distilled under reduced pressure, to obtain 26.2 g (corresponding to 0.211 mol) of 2-amino-5-methoxypyridine (FIG. 1, Step 3).

50 mL of ethyl acetate was added to 28.17 g (corresponding to 126 mmol) of cupric bromide to obtain a suspension, and a solution of 8.18 g (corresponding to 60.0 mmol) of 4'-hydroxyacetophenone in a mixed solution of 50 mL ethyl acetate and 50 mL of chloroform was added thereto. Then, the mixture was refluxed. After five hours, the reaction solution was cooled down to room temperature and filtered. The resulting filtrate was concentrated under reduced pressure. The residue was dissolved in ethyl acetate, and subjected to decoloring operation with addition of active charcoal. Then, the solution was filtered and concentrated. The resulting crude product was purified by flash silica gel column chromatography (elution solvent: chloroform/methanol=20/1). Further, the product was recrystallized from ethyl acetate/petroleum ether, to obtain 7.25 g (corresponding to 33.7 mmol) of 2-bromo-4'-hydroxyacetophenone (FIG. 1, Step 4).

2.15 g (corresponding to 10.0 mmol) of 2-bromo-4'-hydroxyacetophenone and 1.25 g (corresponding to 10.0 mmol) of 2-amino-5-methoxypyridine were dissolved in 50 mL of acetonitrile. The resulting solution was refluxed in an oil bath at 90° C. for 3.5 hours. After the completion of the reaction, the reaction solution was cooled down to room temperature, and precipitates were filtered and recovered. The recovered precipitates were washed with acetonitrile, and dried under reduced pressure to obtain crude crystals. The resulting crude crystals were suspended in a mixed solution of 40 mL of water and 40 mL of methanol. The suspension was supplemented with about 20 mL of a saturated sodium hydrogencarbonate solution, and sonicated for 5 minutes by an ultrasonic washing machine. The precipitates were filtered and recovered from the resulting mixture, washed with water, and dried under reduced pressure, to obtain 1.96 g (corresponding to 8.16 mmol) of 2-(4'-hydroxyphenyl)-6-methoxyimidazo[1,2-a]pyridine (FIG. 1, Step 5).

1.45 mL (corresponding to 20.0 mmol) of 1,3-propanediol was dissolved in 200 mL of methylene chloride. To this solution under an ice bath, 6.96 g (corresponding to 30.0 mmol) of silver oxide, 666 mg (corresponding to 4.0 mmol) of potassium iodide and 4.21 g (corresponding to 22.0 mmol) of p-toluenesulfonyl chloride were added. The resulting mixture was stirred at room temperature for 3 hours. Insoluble matters were filtered out of the reaction mixture, and were washed with ethyl acetate. The washings were combined with the filtrate, and the mixture was concentrated. The resulting crude product was purified with flash silica gel column chromatography (elution solvent: hexane/ethyl acetate=3/2 to 1/1) to obtain 2.47 g (corresponding to 10.7 mmol) of 1,3-propanediol mono-p-toluenesulfonate (FIG. 1, Step 6).

To a solution of 554 mg (corresponding to 2.40 mmol) of 1,3-propanediol mono-p-toluenesulfonate in 10 mL of tetrahydrofuran, 260 mg (corresponding to 1.08 mmol) of 2-(4'-hydroxyphenyl)-6-methoxyimidazo[1,2-a]pyridine and 636 mg (corresponding to 2.42 mmol) of triphenylphosphine were added. Further, 5 mL of N,N-dimethylformamide was added thereto to completely dissolve the contents. To the reaction mixture, 0.48 mL (corresponding to 2.42 mmol) of diisopropylazodicarboxylate was added. After the resulting mixture was stirred at room temperature for 23 hours, the reaction solution was concentrated. The resulting crude product was purified by flash silica gel column chromatography (elution solvent: chloroform/ethyl acetate=19/1), further purified by recycle preparative HPLC (HPLC apparatus: LC-908 (under trade name: manufactured by Japan Analytical Industry Co., Ltd.); column: two of JAIGEL 2H (under trade name; manufactured by Japan Analytical Industry Co., Ltd.) connected together; mobile phase: chloroform), and further purified again by flash silica gel column chromatography (elution solvent: hexane/ethyl acetate=35/65) to obtain 220 mg (corresponding to 0.487 mmol) of 6-methoxy-2-[4'-(3''-p-toluenesulfonyloxypropoxy)phenyl]imidazo[1,2-a]pyridine (FIG. 1, Step 7).

The NMR measurement results of the resulting compound (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 7.81-7.77 (m, 2H), 7.76-7.72 (m, 2H), 7.71-7.70 (m, 1H), 7.64-7.62 (m, 1H), 7.49-7.46 (m, 2H), 7.24-7.21 (m, 2H), 6.95-6.92 (m, 1H), 6.81-6.77 (m, 2H), 4.25 (t, J=6.0 Hz, 2H), 3.95 (t, J=6.0 Hz, 2H), 3.80 (s, 3H), 2.34 (s, 3H), 2.11 (quint., J=6.0 Hz, 2H).

$^{13}$C-NMR (solvent: chloroform-dl, resonance frequency: 125 MHz): δ 158.16, 149.11, 145.41, 144.77, 142.71, 132.64, 129.75, 127.71, 126.93, 126.85, 119.45, 117.28, 114.47, 108.35, 107.49, 66.99, 62.97, 56.11, 28.77, 21.52.

Example 2

Synthesis of 2-[4'-(3''-[$^{18}$F]fluoropropoxy)phenyl]-6-methoxyimidazo[1,2-a]pyridine

[$^{18}$F] Fluoride ion-containing $H_2^{18}O$ (radioactivity 5087 MBq, a value converted at the beginning of synthesis) was passed through a Sep-Pak Light QMA (trade name; manufactured by Japan Waters K.K.) to adsorb and collect the [$^{18}$F] fluoride ions. Then, a potassium carbonate solution (66.7 mmol/L, 0.3 mL) and 1.5 mL of a solution in acetonitrile of 20 mg (corresponding to 53.1 μmol) of Kryptofix 222 (trade name; manufactured by Merck & Co., Inc.) were passed through the column to elute the [$^{18}$F]fluoride ions.

The eluate was heated under helium gas stream to 100° C. to evaporate water, and supplemented with acetonitrile (0.3 mL×2) and azeotropically distilled to dryness. To this, 1.0 mL of a solution in N,N-dimethylformamide of 5 mg of 6-methoxy-2-[4'-(3''-p-toluenesulfonyloxypropoxy)phenyl]imidazo[1,2-a]pyridine synthesized in Example 1. Then, the mixture was heated at 130° C. for 10 hours. After the reaction solution was cooled down to 30° C., it was supplemented with 3.0 mL of diethylether, and passed through a Sep-Pak Plus Silica (trade name; manufactured by Japan Waters K.K.). Then, a mixed solution of 3.5 mL of diethylether and 0.5 ml of N,N-dimethylformamide was passed through the Sep-Pak Plus Silica twice. The diethylether solution that had been passed was heated to 60° C. under helium gas stream and concentrated. The concentrated solution was diluted with 2 mL of a mixed solution of acetonitrile/water/triethylamine=550:450:1.

The resulting solution was purified by HPLC (column: SUMIPAX ODS JP-06 (20 mm i.d.×250 mm, manufactured by Sumika Chemical Analysis Service, Ltd.); elution solvent: acetonitrile/water/triethylamine=500/500/1, flow rate: 7.5 mL/min.). An eluate fraction containing the target compound is diluted with 50 mL of water, and then passed through a Sep-Pak Plus C18 (trade name, manufactured by Japan Waters K.K.) to adsorb and collect the target compound. Then, 20 mL of water was passed through the column to wash it. Then, 2 mL of ethanol was passed through the column to elute a solution in ethanol of 2-[4'-(3''-[$^{18}$F] fluoropropoxy) phenyl]-6-methoxyimidazo[1,2-a]pyridine. The obtained radioactivity was 1795 MBq (94 minutes after the start of synthesis). According to the TLC analysis on the following conditions, the radiochemical purity thereof was 90.4%.

TLC analysis conditions:
TLC plate: Silica Gel 60 $F_{254}$ (under trade name, manufactured by Merck & Co., Inc.)
Mobile phase: chloroform/methanol/triethylamine=50/1/2
Detector: Rita Star (manufactured by Raytest Company)

Examples 3-5, Comparative Examples 1-5

Measurement of Amyloid Affinity

Affinity of the present compounds with amyloid was examined by the following in vitro binding test.

(1) $A\beta_{1-40}$ (Peptide Institute, INC.) (hereinafter referred to as $A\beta_{1-40}$) was dissolved in phosphate buffer (pH 7.4) and shaken at 37° C. for 62-72 hours, to obtain a 1 mg/mL suspension of aggregated $A\beta$ (referred to as amyloid suspension hereinafter in the Examples).

(2) According to the method described in a literature (Naiki, H., et al., Laboratory Investigation 74, p. 374-383 (1996)), the amyloid suspension was subjected to qualitative experiment based on fluorescence spectrophotometric method using Thioflavin T (manufactured by Fluka) to confirm that the aggregated $A\beta$ obtained in (1) was amyloid (measurement conditions: excitation wavelength of 446 nm, and emission wavelength of 490 nm).

(3) According to the method described in a literature (Wang, Y., et al., J. Labelled Compounds Radiopharmaceut. 44, 5239 (2001)), [$^{125}$I]2(3'-iodo-4'-aminophenyl)benzothiazole (hereinafter referred to as [$^{125}$I]3-I-BTA-0) was prepared from a labeling precursor 2-(4'-aminophenyl)benzothiazole, and dissolved in ethanol. As Congo Red, Thioflavin T and 6-methyl-2-[4'-(N,N-dimethylamino)phenyl]benzothiazole (hereinafter referred to as 6-Me-BTA-2), commercially available reagents were weighed and used as they were.

(4) 2-(3'-Iodo-4'-aminophenyl)benzothiazole (hereinafter referred to as 3'-1-BTA-0) and IMPY were synthesized according to the methods described in a literature (Wang. Y., et al., J. Labelled Compounds Radiopharmaceut. 44, S239 (2001)) and a literature (Zhuang, Z. P., et al., J. Med. Chem. 46, 237 (2003)), respectively.

(5) Samples in which [$^{125}$I]3'-1-BTA-0, each compound for evaluation and amyloid were dissolved in a 0.1% bovine serum albumin-containing phosphate buffer (pH 7.4) at final concentrations shown in Table 2 were prepared. The resulting samples were placed in each well (about 0.3 mL in volume) of a 96-well microplate.

TABLE 2

Final concentrations of each compound in sample solutions

| Experiment | Compound for evaluation | Concentration of compound for evaluation | [$^{125}$I]3'-I-BTA-0 concentration | Amyloid |
|---|---|---|---|---|
| Comparative Example 1 | 3'-1-BTA-O | Each concentration of 0, 0.001, 0.01, 0.1, 1, 10, 100, 1000 nmol/L | 400 pmol/L | 1 μmol/L |
| Comparative Example 2 | Congo Red | | | |
| Comparative Example 3 | Thioflavin T | | | |
| Comparative Example 4 | 6-Me-BTA-2 | | | |
| Comparative Example 5 | IMPY | | | |
| Example 3 | Compound 1 | | | |
| Example 4 | Compound 2 | | | |
| Example 5 | Compound 3 | | | |

(6) A microplate filled with a sample solution was shaken at a given rate (400 rotations/min.) at 22° C. for 3 hours. Then, each sample solution was filtered through a glass fiber filter (trade name: Multiscreen™-FC, manufactured by Millipore), to separate the [$^{125}$I]3'-I-BTA-0 attached to amyloid from the [$^{125}$I]3'-BTA-0 free from amyloid.

(7) The glass fiber filter used for the filtration of each sample solution was washed with a 0.1% bovine serum albumin-containing phosphate buffer (pH 7.4) (0.5 mL×five times), and radioactivity of the glass fiber filter was measured with an autowell gamma system (manufactured by Aloka, Type: ARC-301B). The radioactivity was used as the radioactivity level of each sample solution for calculating an inhibition ratio (hereinafter, A denotes the radioactivity level in a sample with zero (0) concentration of each compound for evaluation, and B denotes the radioactivity level in a sample with 0.001 nmol/L or higher concentration of each compound for evaluation).

(8) Separately, a solution containing 15 μmol/L of 6-Me-BTA-2, 400 μmol/L of [$^{125}$I]3'-BTA-0 and 1 μmol/L of $A\beta_{1-40}$ was prepared and subjected to the same procedures as described above in (6) and (7) to measure a radioactivity level. The measured radioactivity level was defined as the background radioactivity level, and used in the calculation of the inhibition ratio (hereinafter referred to as BG).

(9) Using the radioactivity levels measured above in (7) and (8), the inhibition ratio was determined by the following formula (1).

$$\frac{B - BG}{A - BG} \times 100\,(\%) \tag{1}$$

A graph in which values converted by probit transformation from the obtained inhibition ratios were plotted relative to logarithms of concentrations of compounds for evaluation was prepared to obtain an approximate straight line by the least square method. Using the line, the concentration of each compound for evaluation was determined, at which the radioactivity level is half of the level of the sample free from each compound for evaluation, and was defined as a 50% inhibition concentration of each compound (hereinafter referred to as $IC_{50}\%$ value). Using the value as an indicator, affinity of each compound for evaluation with amyloid (aggregated $A\beta_{1-40}$ was evaluated.

$IC_{50\%}$ value of each compound for evaluation is shown in Table 3. Compounds 1 to 3 all showed $IC_{50\%}$ values of less than 100 and had higher affinity with amyloid (aggregated $A\beta_{1-40}$) than Congo Red and Thioflavin T. The results show that Compounds 1 to 3 have good affinity with amyloid (aggregated $A\beta_{1-40}$). In particular, Compound 1 has higher affinity with amyloid (aggregated $A\beta_{1-40}$) than 3'-1-BTA-0 and 6-Me-BTA-2 and had the affinity comparable to IMPY.

TABLE 3

$IC_{50\%}$ values of the present compounds

| Experiment | Compound for evaluation | $IC_{50\%}$ values (nmol/L) |
|---|---|---|
| Comparative Example 1 | 3'-1-BTA-O | 10.1 |
| Comparative Example 2 | Congo Red | >1000 |
| Comparative Example 3 | Thioflavin T | >1000 |
| Comparative Example 4 | 6-Me-BTA-2 | 25.4 |
| Comparative Example 5 | IMPY | 0.8 |
| Example 3 | Compound 1 | 1.1 |
| Example 4 | Compound 2 | 30.5 |
| Example 5 | Compound 3 | 36.6 |

Example 6, Comparative Example 6

Measurement of Partition Coefficient Based on the Octanol Extraction Method

Partition coefficients based on the octanol extraction method (hereinafter referred to as log $P_{octanol}$) were measured, which are generally used as an indicator of permeability of compounds through the blood-brain barrier (hereinafter referred to as BBB).

To 2 mL of octanol, 10 µL of a solution containing Compound 4 (Example 5) and 2 mL of a 10 mmol/L phosphate buffer (pH 7.4) were added and stirred for 30 seconds. After the mixture was centrifuged (2000 rpm×60 min.) with a low-speed centrifuge (model: CENTRIFUGE CT4D manufactured by Hitachi Koki Co., Ltd.), the octanol layer and the water layer were sampled each in an amount of 1 mL, and subjected to measurement of radioactivity with an autowell gamma system (manufactured by Aloka, Type: ARC-301B). Using the obtained radioactivity, log $P_{octanol}$ was calculated in accordance with the equation (2).

$$\log P_{octanol} = \log_{10}\left(\frac{\text{Radioactivity count of octanol layer}}{\text{Radioactivity count of water layer}}\right) \quad (2)$$

The results are shown in Table 4. It is known that compounds permeable to BBB show a log $P_{octanol}$ value between 1 and 3 (Douglas D. Dischino et al., J. Nucl. Med., (1983), 24, p. 1030-1038). Compound 4 showed a log $P_{octanol}$ value of 1.8, and thus it is implied that Compound 4 has a BBB permeability comparable to IMPY of the Comparative Example.

TABLE 4

| log $P_{octanol}$ value of the present compound | | |
|---|---|---|
| Experiment | Compound | log $P_{octanol}$ value |
| Comparative Example 6 | [$^{123}$I]-IMPY | 2.1 |
| Example 6 | Compound 4 | 1.8 |

Examples 7-9, Comparative Example 7

Measurements of Partition Coefficient Based on HPLC

The partition coefficient by HPLC (hereinafter referred to as log $P_{HPLC}$) was measured by the following method. It is known that the log $P_{HPLC}$ shows the same numerical value at a pH of 7.2 to 7.4 as the log $P_{octanol}$ value which is generally known as an indicator of permeability of compounds to BBB (Franco Lombardo et al., J. Med. Chem., (2000), 43, p. 2922-2927).

First, compounds for evaluation shown in Table 5 were dissolved at a concentration of 1 mg/mL in methanol containing 10% dimethylsulfoxide to prepare sample solutions. One µL of the sample solution was subjected to HPLC analysis under the following conditions to determine the elution time ($t_O$) of the solvent and the elution time ($t_R$) of each compound.

TABLE 5

| Compounds for evaluation in experiments | |
|---|---|
| Experiment | Compound for evaluation |
| Comparative Example 7 | IMPY |
| Example 7 | Compound 1 |
| Example 8 | Compound 2 |
| Example 9 | Compound 3 |

HPLC conditions:

Column: Prodigy ODS (3) (product name; manufactured by phenomenex; size: 4.6×250 mm)

Mobile phase: a mixed solution of 50 mM triethylamine phosphate (pH 7.2)/acetonitrile=40/60

Flow rate: 0.7 mL/min.

Detector: ultraviolet visible absorptiometer (detection wavelength: 282 nm)

Using the obtained $t_O$ and $t_R$, the retention factor (hereinafter referred to as K'$_{HPLC}$ value) of each compound for evaluation was determined according to the calculation formula (3).

$$K'_{HPLC} = (t_R - t_0)/t_0 \quad (3)$$

Separately, 10 µL each of a solution of [$^{125}$I]-2-(4'-(3''-fluoropropoxy)phenyl-6-iodoimidazo[1,2-a]pyridine (37 MBq/mL in radioactivity concentration) synthesized above in Reference Example 6 and a solution of [$^{125}$I]-2-(4'-hydroxyphenyl)-6-iodoimidazo[1,2-a]pyridine (37 MBq/mL in radioactivity concentration) synthesized above in Reference Example 7 was added to 2 mL of octanol prepared separately, and 2 mL of 10 mmol/L phosphate buffer (pH 7.4) was further added to the respective solutions. After the individual solutions were stirred for 30 seconds, the solutions were centrifuged at 2,000 rpm for 60 minutes. Radioactivity each of 1 mL of the octanol phase and 1 mL of the water phase was counted by an autowell gamma system (manufactured by Aloka Co., Ltd.: Type ARC-301B). Based on the obtained radioactivity, log $P_{octanol}$ values were calculated according to the above equation (2).

Further, a solution of 2-(4'-(3''-fluoropropoxy)phenyl-6-iodoimidazo[1,2-a]pyridine synthesized above in Reference Example 4 and a solution of 2-(4'-hydroxyphenyl)-6-iodoimidazo[1,2-a]pyridine synthesized above in Reference Example 5 were each subjected to HPLC analysis in the same manner as described above to determine K'$_{HPLC}$ values.

A graph was prepared, in which the log $P_{octanol}$ values of [$^{125}$I]-2-(4'-(3''-fluoropropoxy)phenyl-6-iodoimidazo[1,2-a]pyridine and [$^{125}$I]-2-(4'-hydroxyphenyl)-6-iodoimidazo[1,2-a]pyridine are respectively plotted relative to the log$_{10}$ K'$_{HPLC}$ values of 2-(4'-(3''-fluoropropoxy)phenyl-6-iodoimidazo[1,2-a]pyridine and 2-(4'-hydroxyphenyl)-6-iodoimidazo[1,2-a]pyridine, so that the slope and the intercept on the axis Y of the straight line were determined. Using these values, the following formula (4) was determined, provided that the log $P_{octanol}$ value is equal to the log $P_{HPLC}$ value at a pH of 7.2 to 7.4.

$$\log P_{HPLC} = 0.96(\log K'_{HPLC}) + 1.59 \quad (4)$$

Using K'$_{HPLC}$ obtained for each compound for evaluation, the log $P_{HPLC}$ value of each compound for evaluation was determined according to the above calculation formula (4).

The results are shown in Table 6. As shown in the Table, the log $P_{HPLC}$ values of Compounds 1 through 3 were all between 1 to 3. As mentioned above, it is known that compounds permeable to BBB have a log $P_{octanol}$ value between 1 to 3 (Douglas D. Dischino et al., J. Nucl. Med., (1983), 24, p. 1030-1038). And, it is known that the log $P_{HPLC}$ shows the same value at a pH of 7.2 to 7.4 as the log $P_{octanol}$ (Franco Lombardo et al., J. Med. Chem., (2000), 43, p. 2922-2927). The above-mentioned results imply that Compounds 1 to 3 have a BBB-permeable property.

TABLE 6 logP$_{HPLC}$ value of the present compound

| Experiment | Compound | logP$_{HPLC}$ value |
|---|---|---|
| Comparative Example 7 | IMPY | 2.1 |
| Example 7 | Compound 1 | 1.7 |
| Example 8 | Compound 2 | 1.4 |
| Example 9 | Compound 3 | 1.7 |

Example 10, Comparative Example 8

Measurement of Transferability into Brain and Clearance

Using Compound 4, a time course change of radioactive accumulation in brain of male Wistar rats (7-week old) was measured.

0.05 mL (15-31 MBq/mL in radioactive concentration) of a solution of Compound 4 in a 10 mg/mL ascorbic acid-containing physiological saline solution and a solution of [$^{123}$I]-IMPY (Comparative Example 7) prepared above in Reference Example 8 in a 10 mg/mL ascorbic acid-containing physiological saline solution were each injected under thiopental anesthesia into the tail vein of the rats. The rats were sacrificed by bleeding from abdominal artery, and brains were removed and subjected to measurement of radioactivity (hereinafter referred to as A in this Example) with an autowell gamma system (Type: ARC-301B manufactured by Aloka Co., Ltd.) and further subjected to measurement of mass of brains 2, 5, 30 and 60 minutes after the injection. Also, radioactivity (hereinafter referred to as B in this Example) of 0.05 mL of a 1000-fold diluted solution of the injected solution was measured in the same manner as above. Using these measurement results, radioactive distributions per unit weight of brain (% ID/g) at the respective time points were calculated in accordance with the following formula (5). Three animals were used for experiment at the respective time points.

$$\% \ ID/g = \frac{A}{B \times 1000 \times \text{brain weight}} \times 100 \quad (5)$$

The results are shown in Table 7. As shown in Table 7, Compound 4 showed a concentration higher than $^{123}$I-IMPY at the time point of two minutes after the injection, and then showed a tendency to rapidly clear way in 60 minutes. These results suggest that Compound 4 possesses excellent transferability to brain and rapid clearance from brain comparable to $^{123}$I-IMPY.

TABLE 7

Radioactive concentration in brain of the present compound after intravenous injection (rats)

| | Compound | Radioactive concentration per unit weight (% ID/g) | | | |
|---|---|---|---|---|---|
| | | After 2 min. | After 5 min. | After 30 min. | After 60 min. |
| Example 10 | Compound 4 | 1.36 | 0.93 | 0.23 | 0.13 |
| Comparative Example 8 | $^{123}$I-IMPY | 1.02 | 0.99 | 0.20 | 0.08 |

Example 11

Confirmation of Imaging of Amyloid in Brain

The following experiment was carried out in order to examine whether amyloid in brain can be imaged by the compound of the present invention.

(1) A 1 mg/mL suspension of aggregated Aβ (hereinafter referred to as amyloid suspension in this Example) was obtained by dissolving Aβ$_{1-42}$ (Wako Pure Chemical Industries, Ltd.) in a phosphate buffer (pH 7.4), followed by shaking at 37° C. for 72 hours.

(2) 2.5 μL (corresponding to 25 μg) of the amyloid suspension was injected into an amygdaloid nucleus on one side of a male Wistar rat (7-week old). As a control, 2.5 μL of a phosphate buffered physiological saline solution (pH 7.4) was injected into an amygdaloid nucleus on the other side of the rat. The rats were examined 3 days after the injection of the amyloid suspension and the phosphate buffered physiological saline solution.

(3) Compound 4 was dissolved in a 10 mg/mL ascorbic acid-containing physiological saline solution to obtain a sample solution (84 MBq/mL in radioactivity concentration). This solution was injected into the rat through the tail vein (dosage: 0.5 mL, dosed radioactivity: 42 MBq equivalent).

(4) Brain was removed 30 minutes after the injection to prepare a brain slice of 10 μm in thickness with a microtome (type: CM3050S, manufactured by LEICA). The brain slice was exposed to an imaging plate for 1.5 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (manufactured by NIKON Corporation; type: TE2000-U model; excitation wavelength: 400-440 nm; detection wavelength: 470 nm). Thus, it was confirmed that amyloid was deposited on the slice (FIG. 9b).

FIG. 9 shows images by autoradiogram and Thioflavin T staining of the brain slice of the rat to which amyloid was injected intracerebrally. As shown in FIG. 9, an excellent image was obtained in which there was a marked accumulation of radioactivity in the amygdaloid nucleus on the side to which the amyloid suspension was injected whilst non-specific accumulation is low at the other sites. From the result of Thioflavin T staining in the site where radioactivity accumulated, it was confirmed that Amyloid was present in the accumulation site. On the other hand, no significant accumulation of radioactivity was observed in the amygdaloid nucleus on the side to which the phosphate buffered physiological saline solution was injected, compared with the other sites.

These results suggest that Compound 4 possesses a property of accumulating on intracerebral amyloid, and a capability of imaging intracerebral amyloid.

Example 12 Through 14

Reverse Mutation Test

In order to examine mutagenicity of Compound 1, Compound 2 and Compound 3, reverse mutation test using *Salmonella typhimurium* TA98 and TA100 (hereinafter referred to as Ames test) was conducted.

The test was conducted without addition of S9mix and with addition of S9mix. Dimethylsulfoxide was used as a negative control. A positive control was 2-(2-furyl)-3-(5-nitro-2-furyl)

acrylamide in case S9mix was not added, and 2-aminoanthracene in case S9 mix was added.

The amount of each sample to be added to the test plate was 7 dosages (geometric ratio 4) with the maximum dose being 1250 μg/plate for Compound 1, and 7 dosages (geometric ratio 3) with the maximum dose being 5000 mg/plate for Compound 2 and Compound 3. After a sample to be examined and a strain (TA98 or TA100), or a sample to be examined, S9mix and the strain were mixed together, the mixture was multilayered using soft agar on a medium of a test plate, and then incubated at 37° C. for 48 hours. Judgment was made by counting the number of reverse mutation colonies on the plate after the incubation, and when the number of reverse mutation colonies was not less than two times the number in negative control and showed concentration-dependent increase, mutagenicity was determined to be positive.

The results are shown in Table 8. The numbers of reverse mutation colonies of the respective strains in the group treated with Compounds 1, 2 and 3 were less than two times the number of the negative control, regardless of addition of S9mix. In the groups treated with the positive control, apparent increase of the number of reverse mutation colonies was observed. From the aforementioned results, it is judged that Compounds 1, 2 and 3 are negative in the Ames test and have no mutagenicity.

TABLE 8

Results of Ames test

| | | Mutagenicity | | | |
| | | Without addition of S9mix | | With addition of S9mix | |
| | Compound | TA98 | TA100 | TA98 | TA100 |
| Example 12 | Compound 1 | Negative | Negative | Negative | Negative |
| Example 13 | Compound 2 | Negative | Negative | Negative | Negative |
| Example 14 | Compound 3 | Negative | Negative | Negative | Negative |

INDUSTRIAL APPLICABILITY

The compounds of the invention can be utilized in the field of diagnostic agents.

Figure 1:
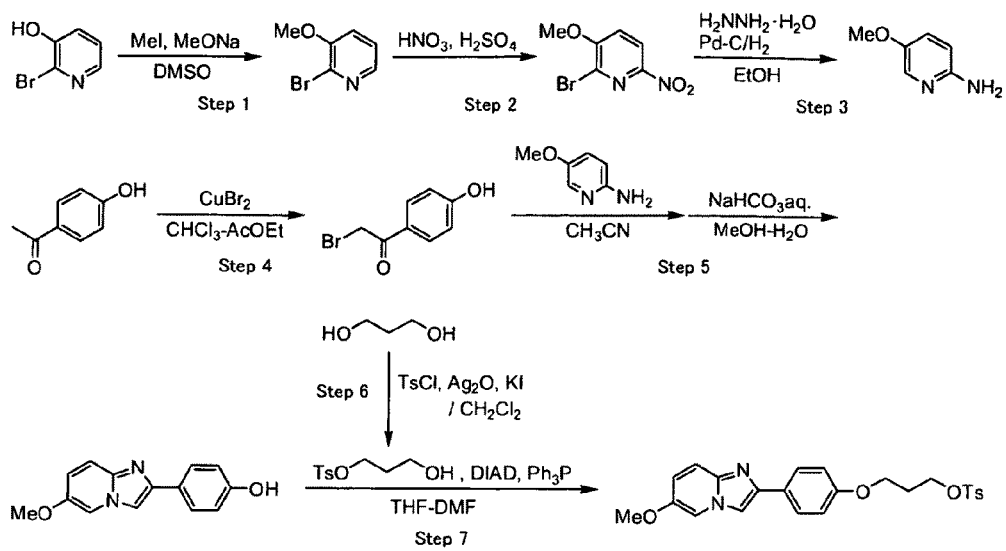
FIG. 1 is a scheme of synthesis of 6-methoxy-2-[4'-(3"-p-toluenesulfonyloxypropoxy)phenyl]imidazo[1,2-a]pyridine.
Figure 2:
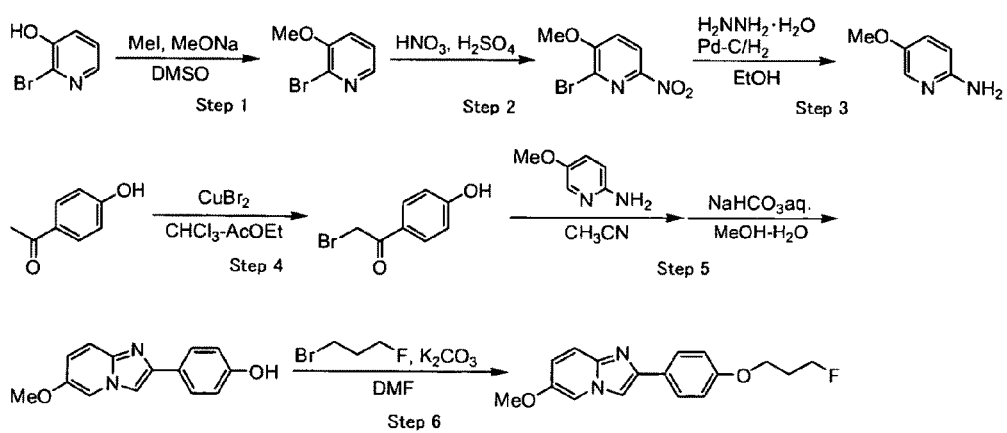
FIG. 2 is a scheme of synthesis of 2-[(4'-(3"-fluoropropoxy)phenyl]-6-methoxyimidazo[1,2-a]pyridine (non-radioactive fluorinated body).
Figure 3:
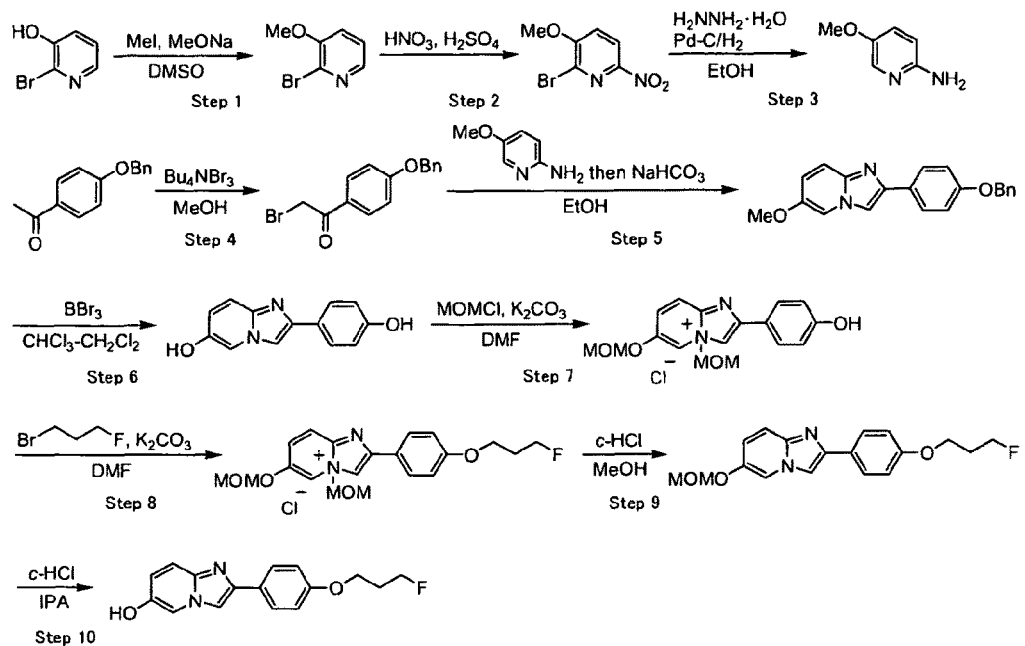
FIG. 3 is a scheme of synthesis of 2-[4'-(3"-fluoropropoxy)phenyl]-6-hydroxyimidazo[1,2-a]pyridine (non-radioactive fluorinated form).
Figure 4:
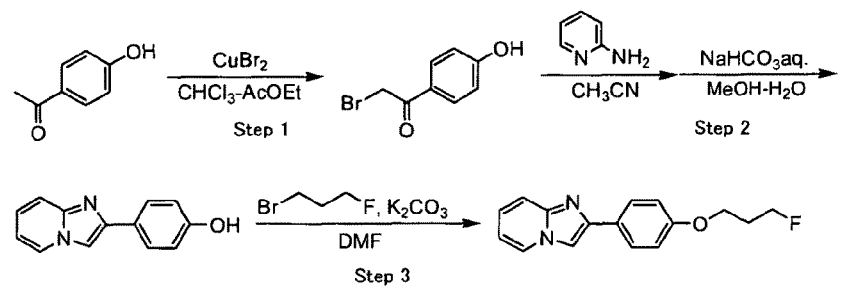
FIG. 4 is a scheme of synthesis of 2-[4'-(3"-fluoropropoxy)phenyl]imidazo[1,2-a]pyridine (non-radioactive fluorinated form).
Figure 5:
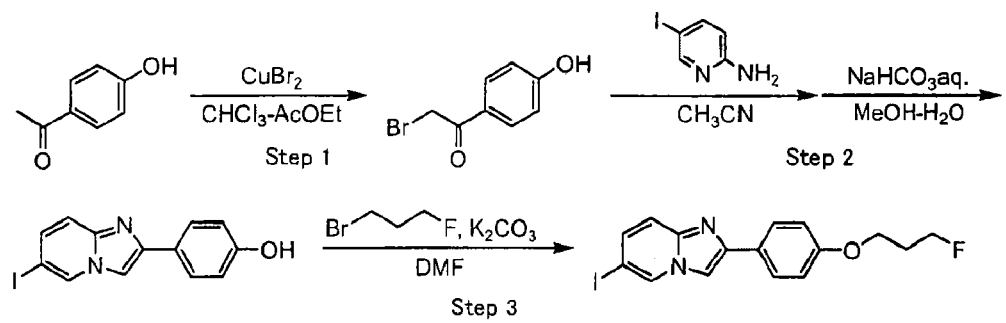
FIG. 5 is a scheme of synthesis of 2-(4'-(3"-fluoropropoxy)phenyl-6-iodoimidazo[1,2-a]pyridine.
Figure 6:
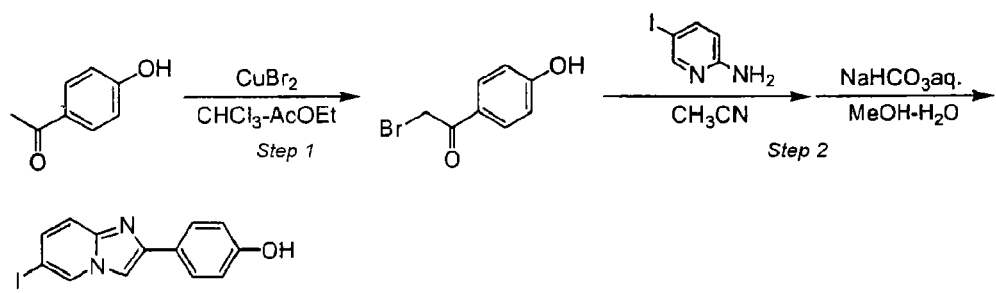
FIG. 6 is a scheme of synthesis of 2-(4'-hydroxyphenyl)-6-iodoimidazo[1,2-a]pyridine.
Figure 7:
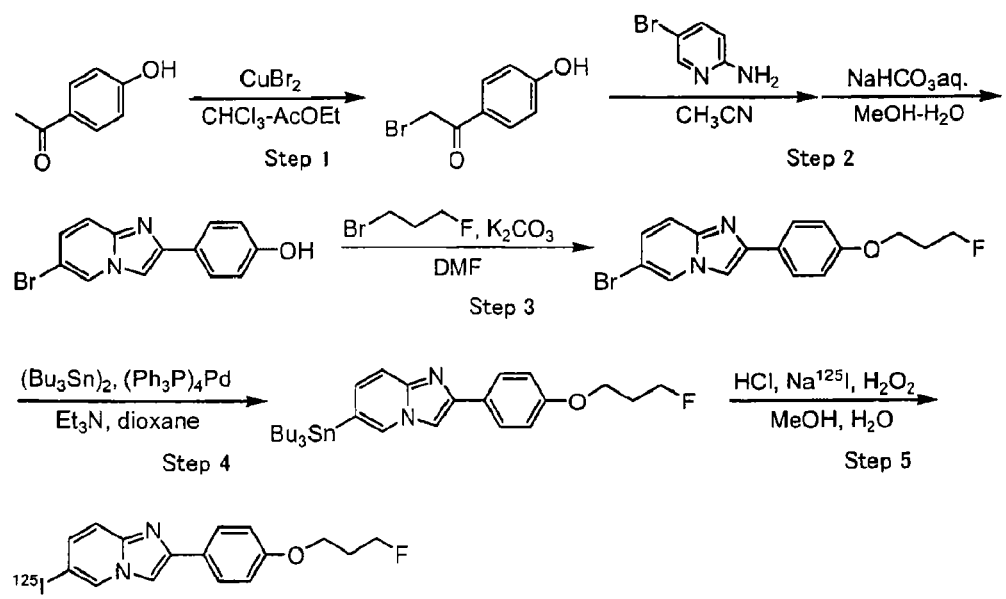
FIG. 7 is a scheme of synthesis of [$^{125}$I]-2-(4'-(3"-fluoropropoxy)phenyl-6-iodoimidazo[1,2-a]pyridine.
Figure 8:
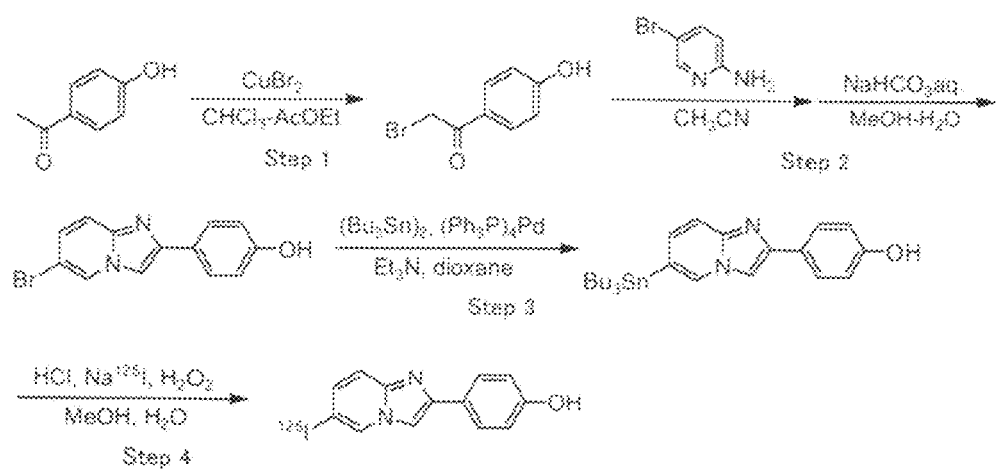
FIG. 8 is a scheme of synthesis of [$^{125}$I]-2-(4'-hydroxyphenyl)-6-iodoimidazo[1,2-a]pyridine.
Figure 9:
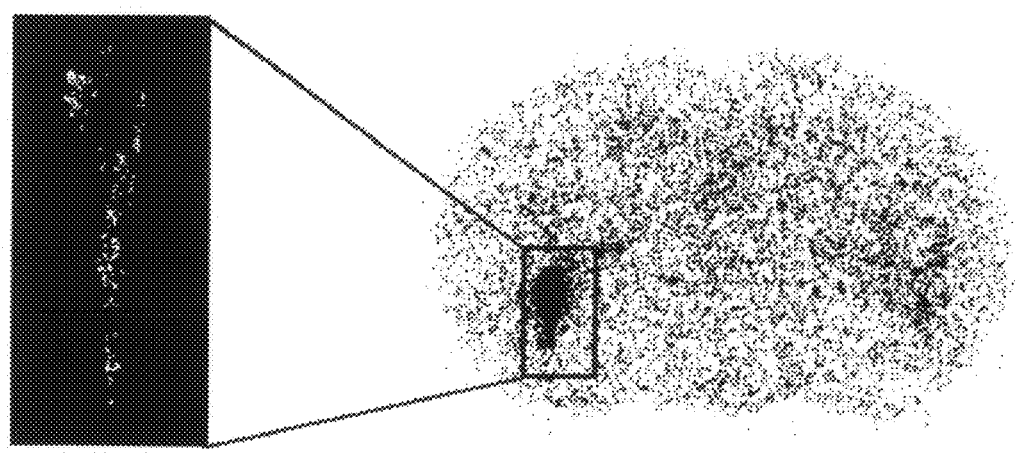
FIG. 9(a) is an autoradiogram of the brain slice 30 minutes after the injection of Compound 4.
FIG. 9(b) is a fluorescent microscopic image of the Thioflavin T stained sample (a magnification of the site to which the amyloid suspension was injected).

The invention claimed is:
1. A compound represented by the following formula (1):

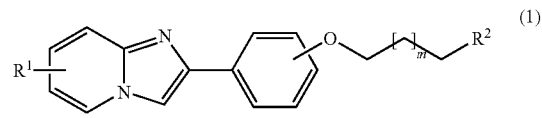

or a salt thereof,
wherein $R^1$ is a group selected from hydrogen, a hydroxyl group, a carboxyl group, a sulfate group, an amino group, a nitro group, a cyano group, an alkyl substituent with 1 to 4 carbon atoms or an alkoxy substituent with 1 to 4 carbon atoms;
$R^2$ is a radioactive halogen substituent; and
m is an integer of 0 to 2.

2. A compound according to claim 1 or a salt thereof, wherein $R^2$ is selected from the group consisting of from $^{18}$F, $^{76}$Br, $^{123}$I, $^{124}$I, $^{125}$I or $^{131}$I.

3. A compound according to claim 1 or a salt thereof, wherein $R^2$ is $^{18}$F.

4. A compound represented by the following formula

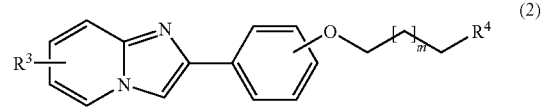

or a salt thereof;
wherein $R^3$ is a group selected from hydrogen, a hydroxyl group, a carboxyl group, a sulfate group, an amino group, a nitro group, a cyano group, an alkyl substituent with 1 to 4 carbon atoms, or an alkoxy substituent with 1 to 4 carbon atoms;
$R^4$ is a group selected from a methanesulfonyloxy substituent, trifluoromethane-sulfonyloxy substituent or aromatic sulfonyloxy substituent; and
m is an integer of 0 to 2.

5. A low-toxic diagnostic agent for Alzheimer's disease, which comprise a compound represented by the following formula (1):

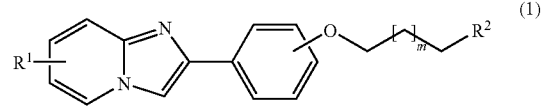

or a salt thereof,
wherein $R^1$ is a group selected from hydrogen, a hydroxyl group, a carboxyl group, a sulfate group, an amino group, a nitro group, a cyano group, an alkyl substituent with 1 to 4 carbon atoms or an alkoxy substituent with 1 to 4 carbon atoms;
$R^2$ is a radioactive halogen substituent; and
m is an integer of 0 to 2.

6. A low-toxic diagnostic agent for Alzheimer's disease, according to claim 5, wherein $R^2$ is selected from the group consisting of from $^{18}F$, $^{76}Br$, $^{123}I$, $^{124}I$, $^{125}I$ and $^{131}I$.

7. A low-toxic diagnostic agent for Alzheimer's disease, according to claim 5, wherein R2 is $18_F$.

8. A pharmaceutical composition for in vivo imaging of amyloid deposits comprising a compound represented by the formula (1) according to claim 1 or a salt thereof, and a pharmaceutically acceptable carrier or excipient.

9. A compound represented by the formula (1) according to claim 1 or a salt thereof for use in medicine.

10. A compound represented by the formula (1) according to claim 1 or a salt thereof for use in in vivo imaging of amyloid deposits.

11. An in vivo method for detecting amyloid deposits in a subject comprising the steps of:

(a) administering a detectable quantity of a compound represented by the formula (1) according to claim 1 or a salt thereof, and (b) detecting the binding of the compound or the salt thereof to amyloid deposit in the subject.

12. A method according to claim 11, wherein step (b) is performed by PET or SPECT imaging.

* * * * *